US 7,250,447 B2

(12) United States Patent
Rawson et al.

(10) Patent No.: US 7,250,447 B2
(45) Date of Patent: Jul. 31, 2007

(54) ACYLSULFAMIDE INHIBITORS OF FACTOR VIIA

(75) Inventors: Thomas E. Rawson, Mountain View, CA (US); Lewis J. Gazzard, Skipton (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/850,312

(22) Filed: May 19, 2004

(65) Prior Publication Data

US 2004/0242585 A1 Dec. 2, 2004

Related U.S. Application Data

(60) Provisional application No. 60/471,804, filed on May 20, 2003.

(51) Int. Cl.
*A61K 31/18* (2006.01)
(52) U.S. Cl. .......................... 514/603; 564/84; 564/86
(58) Field of Classification Search ................ 564/84, 564/86, 79; 514/603, 602
See application file for complete search history.

(56) References Cited

U.S. PATENT DOCUMENTS

| | | | |
|---|---|---|---|
| 3,282,933 A | 11/1966 | Nys et al. |
| 5,399,487 A | 3/1995 | Butenas et al. |
| 5,589,173 A | 12/1996 | O'Brien et al. |
| 5,646,165 A | 7/1997 | Abelman et al. |
| 5,656,600 A | 8/1997 | Abelman et al. |
| 5,656,645 A | 8/1997 | Tamura et al. |
| 5,658,930 A | 8/1997 | Tamura et al. |
| 5,658,939 A | 8/1997 | Abelman et al. |
| 5,670,479 A | 9/1997 | Abelman et al. |
| 5,998,424 A | 12/1999 | Galemmo, Jr. et al. |
| 6,020,357 A | 2/2000 | Pinto et al. |
| 6,034,103 A | 3/2000 | Buckman et al. |
| 6,034,104 A | 3/2000 | Klimkowski et al. |
| 6,140,353 A | 10/2000 | Ackermann et al. |
| 6,358,960 B1 | 3/2002 | Senokuchi et al. |
| 6,410,536 B1 | 6/2002 | Dudley et al. |
| 6,472,393 B1 | 10/2002 | Aliagas-Martin et al. |

FOREIGN PATENT DOCUMENTS

| | | |
|---|---|---|
| DE | 197 18 181 A1 | 11/1998 |
| EP | 0 976 722 | 2/2000 |
| EP | 0 987 274 | 3/2000 |
| WO | WO 93/15756 | 8/1993 |
| WO | WO 94/13693 | 6/1994 |
| WO | WO 96/10022 | 4/1996 |
| WO | WO 96/16940 | 6/1996 |
| WO | WO 96/40679 | 12/1996 |
| WO | WO 97/30073 | 8/1997 |
| WO | WO 98/46591 | 10/1998 |
| WO | WO 98/46626 | 10/1998 |
| WO | WO 98/46627 | 10/1998 |
| WO | WO 98/46628 | 10/1998 |
| WO | WO 00/15658 | 3/2000 |
| WO | WO 00/41531 | 7/2000 |
| WO | WO 03/029226 | 4/2003 |

OTHER PUBLICATIONS

Katakura, S. et al., "A novel factor Xa inhibitor: structure-activity relationships and selectivity between factor Xa and thrombin" *Biochem. & Biophys. Res. Comm.* 197:965-972 (1993).

Lam et al., "Structure-Based Design of Novel Guanidine/ Benzamidine Mimics: Potent and Orally Bioavailable Factor Xa Inhibitors as Novel Anticoagulants" *J. Med. Chem.* 46:4405-4418 (2003).

Lawson, J.H. et al., "A model for the tissue factor pathway to thrombin" *Journal of Biological Chemistry* 269:23357-23366 (1994).

Renatus et al., "Structural and Functional Analyses of Benzamidine-Based Inhibitors in Complex with Trypsin: Implications for the Inhibition of Factor Xa, tPA, and Urokinase" *J. Med. Chem.* 41:5445-5456 (1998).

*Primary Examiner*—Amelia A. Owens
(74) *Attorney, Agent, or Firm*—Min Wang

(57) ABSTRACT

Compounds having the general formula I are useful for inhibiting serine protease enzymes, such as Tissue Factor VIIa, factor Xa, thrombin and kallikrein and have improved permeability properties. These compounds may be used in methods of preventing and/or treating clotting disorders

18 Claims, No Drawings

ACYLSULFAMIDE INHIBITORS OF FACTOR VIIA

This non-provisional application filed under 37 CFR § 1.53(b), claims the benefit under 35 USC § 119(e) of U.S. Provisional Application Ser. No. 60/471,804 filed on May 20, 2003.

FIELD OF THE INVENTION

In one aspect, the invention relates to novel compounds which are inhibitors of Tissue Factor (TF)/factor VIIa, factor VIIa, factor Xa, thrombin and/or kallikrein, as well as compositions containing these compounds. The compounds are useful for inhibiting these factors and for treating disorders mediated thereby. For example, the compounds are useful for preventing thrombosis or treating abnormal thrombosis in a mammal by inhibiting TF/factor VIIa, factor Xa, thrombin and/or kallikrein.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs.

Many significant disease states are related to abnormal haemeostasis. For example, local thrombus formation due to the rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel Furthermore, a high percentage of patients undergoing surgery, particularly in the lower extremities, suffer thrombus formation in the venous vascular system which results in reduced blood flow to the affected area. Each year in the United States, thromboprophylaxis affects approximately 3.3 million patients and deep vein thrombosis occurs in approximately 600,000 patients. Stroke occurs in approximately 5 million patients each year which have episodic atrial fibrillation. Venous thromboembolism, especially in cancer patients, is another manifestation of thrombus disorder.

There continues to be a need for safe and effective therapeutic anticoagulants to limit or prevent thrombus formation.

Blood coagulation is vital for the containment of bodily fluids upon tissue injury and is an important component of host defense mechanisms. Coagulation or clotting involves the sequential activation of multiple zymogens in a process leading to thrombin generation and the conversion of fibrinogen to an impermeable cross-linked fibrin clot. Thrombin production is the result of a blood coagulation cascade which has been intensively studied and increasingly characterized. See for example, Lawson, J. H., et al. (1994) J. Biol. Chem. 269:23357. The coagulation reactions of this cascade involve initiation, amplification and propagation phases. Additionally, the cascade has been divided into extrinsic and intrinsic pathways. The intrinsic pathway involves factors XII, XI, and IX and leads to the formation of a complex of factor IXa with its cofactor, factor VIIIa. This complex converts factor X to Xa. Factor Xa is an enzyme which forms a complex with its cofactor, factor Va, and rapidly converts prothrombin to thrombin. Thrombin converts fibrinogen to fibrin monomers which polymerize to form a clot. The extrinsic pathway involves factor VIIa and tissue factor, which form a complex (TF/factor VIIa), and convert factor X to Xa. As in the intrinsic pathway, factor Xa converts prothrombin to thrombin.

Thrombin (factor IIa), as noted above, occupies a central position in the coagulation cascade by converting fibrinogen to fibrin. Consequently, substantial synthetic efforts have been directed to the development of thrombin inhibitors. See, for example, U.S. Pat. Nos. 5,656,600; 5,656,645; 5,670,479; 5,646,165; 5,658,939; 5,658,930 and WO 97/30073. Additional compounds which have been prepared as synthetic thrombin inhibitors are N-arylsulfinated phenylalanine amides.

Approved anticoagulant therapeutics include orally-administered Warfarin (COUMADIN®) and the subcutaneous injectable LMWH (Low Molecular Weight Heparins). Ximelagatran (EXANTA®) is under development (AstraZeneca) as an oral direct thrombin inhibitor for the prevention and treatment of venous thromboembolism (VTE) and for prevention of stroke in patients with atrial fibrillation. Known inhibitors of factor Xa include bisamidine compounds (Katakura, S. (1993) Biochem. Biophys. Res. Commun., 197:965) and compounds based on the structure of arginine (WO 93/15756; WO 94/13693). Phenyl and naphthylsulfonamides have also been shown to be factor Xa inhibitors (WO 96/10022; WO 96/16940; WO 96/40679).

TF/factor VIIa is a serine protease complex that participates in blood coagulation by activating factor X and/or factor IX. Factor VIIa is produced from its precursor, factor VII, which is synthesized in the liver and secreted into the blood where it circulates as a single chain glycopeptide. The cDNA sequence for factor VII has been characterized (Hagen et al., 1986, Proc. Natl. Acad. Sci. U.S.A., 83:2412–2416).

A variety of natural and synthetic inhibitors of TF/factor VIIa are known and have varying potency and selectivity. Tissue factor pathway inhibitor (TFPI; Broze, 1995, Thromb. Haemostas., 74:90) and nematode anticoagulant peptide c2 (NAPc2; Stanssens et al., 1996, Proc. Natl. Acad. Sci. U.S.A., 93:2149) bind factor Xa prior to the formation of a quaternary inhibitory complex with the TF/factor VIIa complex. Small protein direct inhibitors (Dennis et al, 1994, J. Biol. Chem., 35:22137) and inactive forms of TF/factor VIIa are also known (Kirchhofer et al, 1995, Arteriosclerosis, Thrombosis and Vascular Biol., 15:1098; Jang et al, 1995, Circulation, 92:3041). Additionally, synthetic peptides and soluble forms of mutant TF which retain binding affinity but have reduced cofactor activity have been prepared (Roenning et al, 1996, Thromb. Res., 82:73; Kelley et al, 1997, Blood, 89:3219). U.S. Pat. No. 5,679,639 describes polypeptides and antibodies which inhibit serine protease activity. U.S. Pat. No. 5,580,560 describes a mutant factor VIIa which has an improved half-life. U.S. Pat. No. 5,504,067 and U.S. Pat. No. 5,504,064 describe a truncated TF for the treatment of bleeding. Kunitz domain-tissue factor fusion proteins have also been shown to be bifunctional anticoagulants (Lee et al, 1997, Biochemistry, 36:5607–5611). The TF/factor VIIa complex has been indicated as an attractive target for the development of inhibitors based on a dissociation between surgical bleeding and prevention of intravascular thrombosis (Harker et al, 1995, Thromb. Haemostas., 74:464).

Compounds which block or inhibit enzymes in the coagulation cascade are therapeutically useful in treating or preventing thrombosis in a mammal suspected of having a condition characterized by abnormal thrombosis. For example, with respect to arterial vasculature, abnormal thrombus formation due to deterioration of an established atherosclerotic plaque is a major cause of acute myocardial infarction and unstable angina. Treatment of an occlusive coronary thrombus by thrombolytic therapy or percutaneous transluminal coronary angioplasty (PTCA) may be accompanied by reclosure of the vessel. In the venous vasculature, many patients undergoing surgery, particularly in the abdominal and lower body regions, experience thrombus formation which reduces blood flow and can lead to a pulmonary embolism. Disseminated intravascular coagulopathy in both the venous and arterial systems occurs commonly during septic shock, some viral infections, and cancer and may lead to rapid and widespread thrombus formation and organ failure.

Coumarin type, e.g. Warfarin, have certain therapeutic limitations, including excessive bleeding (minor and major hemorrhage. The typically slow onset of action (prothrombic) and long duration of action also complicate emergency procedures and necessitates frequent monitoring (Levine et al (1995) Chest 108 (4S), 276S; Lafata et al (2000) Thrombosis and Thrombolytics 9: S13; Marchetti et al (2001) Am. J. Med. 111:130; Garcia-Zozaya, I. (1998) J. of Kent. Med. Assoc. 96(4): 143). Also, typically the cost of monitoring blood levels far exceeds the cost of coumarin and heparin type anticoagulant therapy.

PTCA and recanalization are favored procedures for treating occluded vessels. However, arterial thrombosis following these procedures remains a leading cause of failure. Heparin, the most widely used anticoagulant, has not been shown to be entirely effective in the treatment and prevention of acute arterial thrombosis or rethrombosis.

The synthesis and development of small molecule inhibitors based on the known three-dimensional structure of proteins is a challenge of modern drug development. Many thrombin inhibitors have been designed to have a hirudin-type structure. Stubbs and Bode, *Current Opinion in Structural Biology* 1994, 4:823–832. New synthetic thrombin inhibitors, as well as inhibitors of factor Xa and TF/factor VIIa, are reported. See, for example, *Annual Reports in Medicinal Chemistry*, 1995–1997, Academic Press, San Diego, Calif.; U.S. Pat. No. 5,589,173 and U.S. Pat. No. 5,399,487.

U.S. Pat. No. 6,472,393 and WO 00/41531 describe a class of inhibitors of serine proteases such as TF/factor VIIa, and which have acylsulfonamide and benzamidine moieties. These serine protease inhibitors have proven to have potent antithrombotic activity in vivo. However, there remains a need for potent TF/factor VIIa inhibitors that have optimized activity, selectivity and pharmacokinetic properties such as clearance, half life and bioavailability. Prodrug forms of TF/factor VIIa inhibitors may be employed to establish improved oral bioavailability.

SUMMARY OF THE INVENTION

An aspect of the present invention is novel compounds which inhibit factors/enzymes in the coagulation cascade and which are useful to prevent or treat thrombus formation in arterial or venous vessels. These compounds are useful as coagulation factor inhibitors and as anticoagulants in general.

In one embodiment, the compounds of the invention selectively inhibit TF/factor VIIa, Xa, or kallikrein.

One aspect of the invention is to provide methods of inhibiting TF/factor VIIa, Xa or thrombin activity by contacting these enzymes with an effective inhibitory amount of the novel inhibitors of the present invention or a composition containing these compounds. A further object is to provide a method of treating a TF/factor VIIa, Xa or thrombin mediated disorder by administering to a mammal in need of such treatment an effective amount of one of the compounds of the invention or a composition containing the compound. An additional object is to provide a method of preventing thrombosis or treating abnormal thrombosis by administering to a mammal in need of such treatment an effective amount of one of the compounds of the invention or a composition containing the compound and a carrier or excipient.

These and other objects which will become apparent in the course of the following description have been achieved by the acylsulfamide compounds of the present invention having the general formula I:

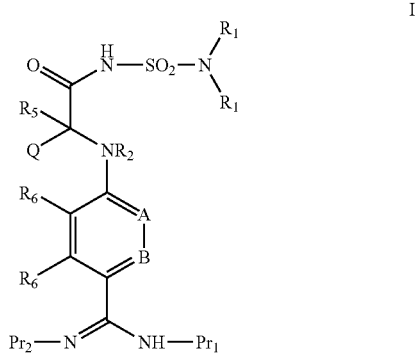

wherein

A and B are independently CH, $CR_3$ or N;

Q is:

(1) optionally substituted alkyl having 1 to about 10 carbon atoms;

(2) optionally substituted aralkyl containing an aryl moiety having 6 to about 10 ring carbon atoms bonded to an alkyl moiety containing 1 to about 10 carbon atoms;

(3) optionally substituted heteroaralkyl containing a heteroaryl moiety having 5 to about 10 ring atoms bonded to an alkyl moiety having 1 to about 10 carbon atoms;

(4) optionally substituted carbocycloalkyl containing a carbocyclic moiety having 3 to about 10 ring carbon atoms bonded to an alkyl moiety having 1 to about 10 carbon atoms;

(5) optionally substituted heterocycloalkyl containing a heterocyclic moiety having 3 to about 10 ring atoms bonded to an alkyl moiety having 1 to about 10 carbon atoms;

(6) optionally substituted alkenyl having 2 to about 10 carbon atoms;

(7) optionally substituted aralkenyl containing an aryl moiety having 5 to about 10 ring atoms bonded to an alkenyl moiety having 2 to about 10 carbon atoms;

(8) optionally substituted heteroaralkenyl containing a heteroaryl moiety having 5 to about 10 ring atoms bonded to an alkenyl moiety having 2 to about 10 carbon atoms;

(9) optionally substituted carbocycloalkenyl containing a carbocyclic moiety having 3 to about 10 ring carbon atoms bonded to an alkenyl moiety having 2 to about 10 carbon atoms;

(10) optionally substituted heterocycloalkenyl containing a heterocyclic moiety having 3 to about 10 ring atoms bonded to an alkenyl moiety having 2 to about 10 carbon atoms;

(11) optionally substituted aryl having 6 to about 10 ring carbon atoms;

(12) optionally substituted heteroaryl having 5 to about 10 ring atoms with ring atoms selected from carbon atoms and heteroatoms, where the heteroatoms are nitrogen, oxygen or sulfur;

(13) optionally substituted carbocyclic having 3 to about 10 ring carbon atoms;

(14) optionally substituted heterocyclic having 3 to about 10 ring atoms with ring atoms selected from carbon atoms and heteroatoms, where the heteroatoms are nitrogen, oxygen or sulfur;

$Pr_1$ and $Pr_2$ are independently H, hydroxy, alkyl, alkoxy, alkanoyl, alkanoyloxy, alkoxycarbonyl, aryloxy, or arylalkoxy;

said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, a carbocycle or a heterocycle;

said carbocycle and heterocycle are optionally substituted with 1–5 hydroxy, alkoxy, carboxyl, alkyl, or halosubstituted alkyl; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—;

each $R_1$ is, independently, H, alkyl, substituted alkyl, aryl, substituted aryl, $C(O)R_7$ or $C(NH)R_7$, or both $R_1$ form a heterocycle optionally substituted with hydroxy, amino, halogen, carboxy alkyl, alkoxy, alkanoyl or alkanoyloxy;

$R_2$ is H, alkyl or substituted alkyl;

$R_3$ is H, $C_1$–$C_6$ alkyl, $C_1$–$C_6$ alkoxy, halogen or OH;

$R_5$ is selected from the group consisting of H, unsubstituted or substituted alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7$, $OC(O)R_7$, $C(O)OR_7$, $C(O)R_7$ and members in which the alkyl, $R_7$ or $R_8$ is substituted with 1–3 F, Cl, Br, I, $OR_7$, $SR_7$, $NR_7R_8$, $OC(OR_7)$, $C(O)OR_7$, $C(O)R_7$, $C(O)NR_7R_8$, $NHC(NH)NH_2$, $PO_3$, unsubstituted or substituted indolyl or unsubstituted or substituted imidazolyl groups;

each $R_6$ is independently H, $C_1$–$C_6$ alkyl, $C_1$–$C_6$ alkyl-$OR_7$, $C_1$–$C_6$ alkyl-$NR_7R_8$, $C_1$–$C_6$ haloalkyl, halo, cyano, $OR_7$, $SR_7$, $NR_7R_8$, $C(O)OR_7$, $C(O)R_7$ or $OC(O)R_7$;

$R_7$ and $R_8$ are independently H or $C_1$–$C_6$ alkyl; and acid and base addition salts, solvates and prodrugs thereof.

Prodrug forms of Formula I compounds, e.g. where $Pr_1$ and/or $Pr_2$ forms a prodrug moiety, may possess improved pharmacokinetic, e.g. oral bioavailability, properties.

Additionally, the objects of the invention are achieved by compositions containing these compounds and the methods described below.

DETAILED DESCRIPTION OF THE INVENTION

Definitions

The terms "factor VIIa", "TF/factor VIIa", "Tissue factor VIIa", "factor Xa", "thrombin" or "kallikrein" relating to a disorder mean a disease or physiological condition involving clotting of the blood and in which inhibition of one or more of these enzymes reduces or eliminates at least one of the physiological symptoms of the disease or condition.

The term "thrombosis" means the development of or formation of a blood clot or thrombus in a blood vessel of a mammal or in a synthetic vessel, such as a plastic or glass tube or vial. A thrombus which has detached from its original site and is found in another site is called a thrombotic embolus.

The term "abnormal thrombosis" means thrombosis occurring in a mammal which is contrary to the good health of the mammal.

The term "alkyl", used alone or as part of another term, means a branched or unbranched, saturated aliphatic hydrocarbon group, having the number of carbon atoms specified, or if no number is specified, having up to and including 12 carbon atoms, represented as $C_n$–$C_m$ alkyl, or where n and m are specified as integers. Examples of alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$–$C_6$ alkyl" and "alkyl of 1 to 6 carbon atoms" are synonymous and used interchangeably. "$C_1$–$C_6$ alkyl" groups include methyl, ethyl, 1-propyl, isopropyl, 1-butyl and sec-butyl.

The terms "substituted alkyl" or "substituted $C_n$–$C_m$ alkyl" where m and n are integers identifying the range of carbon atoms contained in the alkyl group, denotes the above alkyl groups that are substituted by one, two or three halogen (F, Cl, Br, I), trifluoromethyl, hydroxy, unsubstituted and substituted $C_1$–$C_7$ alkoxy, protected hydroxy, amino (including alkyl and dialkyl amino), protected amino, unsubstituted and substituted $C_1$–$C_7$ acyloxy, unsubstituted and substituted $C_3$–$C_7$ heterocyclic, unsubstituted and substituted phenoxy, nitro, carboxy, protected carboxy, unsubstituted and substituted carboalkoxy, unsubstituted and substituted acyl, carbamoyl, carbamoyloxy, cyano, methylsulfonylamino, unsubstituted and substituted benzyloxy, unsubstituted and substituted $C_3$–$C_6$ carbocyclic or $C_1$–$C_4$ alkoxy groups. The substituted alkyl groups may be substituted once, twice or three times with the same or with different substituents.

Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, trifluoroethyl, trifluoropropyl, carboxypropyl, 2-aminopropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocyclic group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. An exemplary group includes the substituted methyl group, e.g. a methyl group substituted by the same substituents as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

The term "alkoxy" denotes groups having the number of carbon atoms specified such as methoxy, ethoxy, n-propoxy, isopropoxy, n-butoxy, s-butoxy, t-butoxy and like groups.

Alkoxy groups may be represented as RO—, where R is an $C_n$–$C_m$ alkyl group. The term "substituted alkoxy" means these alkoxy groups substituted by the same substituents as the "substituted $C_n$–$C_m$ alkyl" group, for example, 2,2,2-trifluoroethoxy, 2,2,2-trifluoropropoxy, etc.

The term "acyloxy" denotes herein carboacyloxy groups having the specified number of carbon atoms such as formyloxy, acetoxy, propionyloxy, butyryloxy, pentanoyloxy, hexanoyloxy, heptanoyloxy, and the like. Acyloxy groups may be represented as RC(O)O—, where R is H or an $C_n$–$C_m$ alkyl group. The term "substituted acyloxy" means these acyloxy groups substituted by the same substituents as the "substituted $C_n$–$C_m$ alkyl" group.

The term "alkylcarbonyl", "alkanoyl" and "acyl" are used interchangeably herein encompass groups having the specified number of carbon atoms such as formyl, acetyl, propionyl, butyryl, pentanoyl, hexanoyl, heptanoyl, benzoyl and the like.

The terms "carbocyclic", "carbocyclyl" and "carbocyclo" alone and when used as a moiety in a complex group such as a carbocycloalkyl group, refers to a mono-, bi-, or tricyclic aliphatic ring having 3 to 14 carbon atoms, e.g. 3 to 7 carbon atoms. Carbocyclic groups include cyclopropyl, cyclobutyl, cyclopentyl and cyclohexyl groups. The terms "substituted carbocyclic" and "carbocyclo" mean these groups substituted by the same substituents as the "substituted $C_n$–$C_m$ alkyl" group.

A "carbocycloalkyl" group is a carbocyclo group as defined above covalently bonded to an alkyl group as defined above.

The term "alkenyl" means a branched or unbranched hydrocarbon group having the number of carbon atoms designated containing one or more carbon-carbon double bonds, each double bond being independently cis, trans, or a nongeometric isomer. The term "substituted alkenyl" means these alkenyl groups substituted by the same substituents as the "substituted $C_n$–$C_m$ alkyl" group.

The term "alkynyl" means a branched or unbranched hydrocarbon group having the number of carbon atoms designated containing one or more carbon-carbon triple bonds. The term "substituted alkynyl" means these alkynyl groups substituted by the same substituents as the "substituted $C_n$–$C_m$ alkyl" group.

The terms "alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone or as part of another term means a homocyclic aromatic group whether or not fused having the number of carbon atoms designated or if no number is designated, up to 14 carbon atoms. Aryl groups, "Ar", include phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]).

The term "aryloxy" denotes a group which comprises an aryl group and an oxygen atom. Aryloxy groups may be represented as ArO—. Examples of aryloxy include phenoxy (($C_6H_5O$—, PhO—)

The term "arylalkoxy" denotes a group which comprises an aryl group, an alkyl group and an oxygen atom Arylalkoxy groups may be represented as Ar—($C_n$–$C_m$ alkyl)-O—. Examples of arylalkoxy include benzyloxy ($C_6H_5CH_2O$—, BnO—).

The term "substituted phenyl" or "substituted aryl" denotes a phenyl group or aryl group substituted with one, two, three, four or five, configured for example as 1–2, 1–3 or 1–4 substituents chosen from halogen (F, Cl, Br, I), hydroxy, protected hydroxy, cyano, nitro, alkyl (e.g. $C_1$–$C_6$ alkyl), alkoxy (e.g. $C_1$–$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclic, aryl, or other groups specified. One or methyne (CH) and/or methylene ($CH_2$) groups in these substituents may in turn be substituted with a similar group as those denoted above. Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di($C_1$–$C_6$ alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3,4-diethoxyphenyl, 3-ethoxy-4-isopropoxyphenyl, 3-ethoxy-s-butoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where 1, 2, or 3 of the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Exemplary substituted phenyl groups include the 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Also, the term "substituted phenyl" represents phenyl groups having an aryl, phenyl or heteroaryl group fused thereto. The fused ring may also be substituted with any, e.g. 1, 2 or 3, of the substituents identified above for "substituted alkyl" groups.

The term "aralkyl" means one, two, or three aryl groups having the number of carbon atoms designated, appended to an alkyl group having the number of carbon atoms designated including but not limited to; benzyl ($C_6H_5CH_2$—, Bn—), napthylmethyl, phenethyl ($C_6H_5CH_2CH_2$—), benzhydryl (diphenylmethyl), trityl, and the like. One exemplary arylalkyl group is the benzyl group. Aralkyl groups may be represented as Ar—($C_n$–$C_m$ alkyl)-.

The term "substituted aralkyl" denotes an alkyl group, such as a $C_1$–$C_8$alkyl group, substituted at any carbon with an aryl group, e.g. a $C_6$–$C_{10}$ aryl group, bonded to the alkyl group through any aryl ring position and substituted on the alkyl portion with one, two or three groups chosen from halogen (F, Cl, Br, I), hydroxy, protected hydroxy, amino, protected amino, $C_1$–$C_7$acyloxy, nitro, carboxy, protected carboxy, carbamoyl, carbamoyloxy, cyano, $C_1$–$C_6$alkylthio, N-(methylsulfonylamino) or $C_1$–$C_4$alkoxy. Optionally the aryl group may be substituted with one, two, three, four or five groups chosen from halogen, hydroxy, protected hydroxy, nitro, $C_1$–$C_6$ alkyl, $C_1$–$C_6$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_8$ alkyl portion or the aryl portion or both are disubstituted, the substituents can be the same or different. This group may also appear as the substituted aralkyl moiety of a substituted aralkoxy group.

Examples of the term "substituted aralkyl" and this group when it occurs in a "substituted aralkoxy" group include groups such as 2-phenyl-1-chloroethyl, 1-phenyl-1-chloromethyl, 1-phenyl-1-bromomethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy (n-hexyl), 5-(4-aminomethyl phenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as methyl, ethyl, isopropyl, t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Carboxylic acid protecting groups include allyl and p-nitrobenzyl groups. Similar carboxy-protecting groups used in the cephalosporin, penicillin and peptide arts can also be used to protect a carboxy group substituents. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

The terms "heterocyclic group", "heterocyclic", "heterocyclic", or "heterocyclo" alone and when used as a moiety in a complex group such as a heterocycloalkyl group, are used interchangeably and refer to any mono-, bi-, or tricyclic saturated or non-aromatically unsaturated ring having the number of atoms designated, generally from 3 to about 10 ring atoms, where the ring atoms are carbon and 1, 2, 3 or 4 nitrogen, sulfur or oxygen atoms. Typically, a 5-membered ring has 0 to 2 double bonds and 6- or 7-membered ring has 0 to 3 double bonds and the nitrogen or sulfur heteroatoms may optionally be oxidized, and any nitrogen heteroatom may optionally be quaternized. Examples include pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperidinyl, and 3,4,5,6-tetrahydropiperidinyl.

A "heterocycloalkyl" or a "heterocycloalkenyl" group is a heterocyclo group as defined above covalently bonded to an alkyl or alkenyl group as defined above.

Unless otherwise specified, "heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and e.g. where at least one heteroatom is nitrogen (*Lang's Handbook of Chemistry*, supra). Included in the definition are any bicyclic groups where any of the above heteroaryl rings are fused to a benzene ring.

The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl.

Heterocyclic 5-membered ring systems containing a sulfur or oxygen atom and one to three nitrogen atoms are also suitable for use in the instant invention. Examples of heterocyclic groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, such as oxazol-2-yl, and oxadiazolyl, such as 1,3,4-oxadiazol-5-yl, and 1,2,4-oxadiazol-5-yl. A group of further examples of 5-membered ring systems with 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. One group of examples of benzo-fused derivatives are benzoxazol-2-yl, benzthiazol-2-yl and benzimidazol-2-yl.

Further suitable specific examples of the above heterocyclic ring systems are 6-membered ring systems containing one to three nitrogen atoms. Such examples include pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are an exemplary group.

The substituents for the optionally substituted heterocyclic ring systems, and further examples of the 5- and 6-membered ring systems discussed above can be found in W. Druckheimer et al., U.S. Pat. No. 4,278,793.

An exemplary group of "heteroaryl" includes; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy 4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-astriazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

A "heteroaralkyl" or a "heteroaralkenyl" group is a heteroaryl group as defined above covalently bonded to an alkyl group or to an alkenyl group as defined above.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, aralphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Organic nontoxic bases include isopropylamine, diethylamine, ethanolamine, trimethamine, dicyclohexylamine, choline, and caffeine.

The term "prodrug" as used herein means a derivative of a parent drug molecule that enhances pharmaceutically desirable characteristics or properties (e.g. transport, bioavailability, pharmacodynamics, etc.) and that requires biotransformation, either spontaneous or enzymatic, within the organism to release the active parent drug.

Embodiments

The invention provides compounds which inhibit factor VIIa and exhibit unexpected and improved pharmacokinetic properties. Compounds of the invention may have improved clearance and/or half life in vivo.

In an embodiment of the invention there is provided compounds which specifically inhibit TF/factor VIIa, relative to the inhibition of factor Xa, thrombin or kallikrein.

In another embodiment there is to provided a method of inhibiting TF/factor VIIa, Xa or thrombin activity by contacting these enzymes with an effective inhibitory amount of the novel inhibitors of the present invention or a composition containing these compounds. A further object is to provide a method of treating a TF/factor VIIa mediated disorder by administering to a mammal in need of such treatment an effective amount of one of the compounds of the invention or a composition containing the compound. An additional object is to provide a method of preventing thrombosis or treating abnormal thrombosis by administering to a mammal in need of such treatment an effective amount of one of the compounds of the invention or a composition containing the compound and a diluent, carrier or excipient.

The invention is generally directed to acylsulfamide inhibitors of factor VIIa which exhibit unexpected and improved permeability and/or bioavailability properties, said inhibitors having the general formula I:

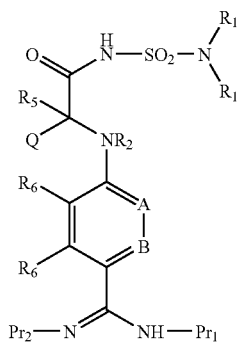

wherein $R_1$, $R_5$, $R_6$, A, B, Q, $Pr_1$ and $Pr_2$ have the meanings described above. In these meanings, alkyl is unsubstituted or substituted $C_1$–$C_6$ alkyl; alkenyl is unsubstituted or substituted $C_2$–$C_6$ alkenyl; alkynyl is unsubstituted or substituted $C_2$–$C_6$ alkynyl; aryl is unsubstituted or substituted naphthyl or phenyl; aralkyl is unsubstituted or substituted benzyl.

Each $R_1$ is, independently, H, alkyl, substituted alkyl, $C(O)R_7$ or $C(NH)R_7$, or both $R_2$ substituents together form a heterocycle optionally substituted with hydroxy, amino, halogen, carboxy alkyl, alkoxy, alkanoyl or alkanoyloxy. In one embodiment $R_1$ is H, alkyl, aralkyl, including methyl, ethyl, propyl, benzyl. In another embodiment, both $R_1$ are H or methyl. Alternatively both $R_1$ substituents together with the nitrogen atom from which they depend form a morpholino heterocycle.

$R_5$ is selected from the group consisting of H, unsubstituted or substituted alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7$, $OC(O)R_7$, $C(O)OR_7$, $C(O)R_7$ and members in which the alkyl, $R_7$ or $R_8$ is substituted with 1–3 F, Cl, Br, I, $OR_7$, $SR_7$, $NR_7R_8$, $OC(OR_7)$, $C(O)OR_7$, $C(O)R_7$, $C(O)NR_7R_8$, $NHC(NH)NH_2$, $PO_3$, unsubstituted or substituted indolyl or unsubstituted or substituted imidazolyl groups. In a particular embodiment $R_5$ is H.

Each $R_6$ is independently H, $C_1$–$C_6$ alkyl, $C_1$–$C_6$ alkyl-$OR_7$, $C_1$–$C_6$ alkyl-$NR_7R_8$, $C_1$–$C_6$ haloalkyl, halo, cyano, $OR_7$, $SR_7$, $NR_7R_8$, $C(O)OR_7$, $C(O)R_7$ or $OC(O)R_7$. In another embodiment, one $R_6$ on the benzamidine ring is H while the other is F. In another embodiment, both $R_6$ on the benzamidine ring are H.

In another embodiment, $Pr_1$ and $Pr_2$ are independently a prodrug group which enhances the permeability of the compound and therefore bioavailability and is cleaved upon uptake to provide a free amidine group. $Pr_1$ and $Pr_2$ are independently H, hydroxy, alkyl, alkoxy, alkanoyl, alkanoyloxy, alkoxycarbonyl, aryloxy, or arylalkoxy; where alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, a carbocycle or a heterocycle; and where carbocycle and heterocycle are optionally substituted with 1–5 hydroxy, alkoxy, carboxyl, alkyl, or halosubstituted alkyl; and whereone to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—.

By "replace" is meant that a carbon atom and pending hydrogen atoms (e.g. a methylene group) of the aliphatic portion of an alkyl, alkoxy, alkanoyl etc. group is substituted with one of the specified atoms or divalent groups. For example, substituting a methylene group for an oxygen atom in an alkyl chain forms an ether. In another embodiment, $Pr_2$ is H while $Pr_1$ is selected from the specified groups. In another embodiment, $Pr_1$ is hydroxy or alkoxy, or alkanoyl optionally substituted with halogen, such as Cl; or trisubstituted with F. In another embodiment, $Pr_1$ is 2-trichloroethyloxycarbonyl. $Pr_1$ groups may be hydroxy and ethoxy. In another embodiment $Pr_1$ incorporates a carbocycle and is selected from the group consisting of aryloxy, arylcarbonyl, arylcarbonyloxy, arylalkoxy, arylalkoxycarbonyl, arylalkanoyl or arylalkanoyloxy. Exemplary $Pr_1$ groups of this type are benzyl, substituted benzyl, benzoyl, benzoyl substituted with 1 or 2 $CF_3$ groups, benzoyloxy substituted with 1 or 2 $CF_3$ groups. In one embodiment, $Pr_1$ is phenoxy, benzyl substituted at both meta positions with $CF_3$ (i.e. 3,5-disubstituted), benzyl substituted at both a meta and para position with $CF_3$ (i.e. 3,4,-disubstituted) benzyl substituted at both an ortho and meta position (i.e. 2,3-disubstituted), or benzyloxycarbonyl substituted with $CF_3$ (2,3-3,4- or 3,5-disubstituted). Alternatively, $Pr_1$ is H while $Pr_2$ is selected from one of the specified groups. In such an embodiment $Pr_2$ is alkoxy, such as methoxy, ethoxy, or allyloxy.

Q is:
(1) optionally substituted alkyl having 1 to about 10 carbon atoms;
(2) optionally substituted aralkyl containing an aryl moiety having 6 to about 10 ring carbon atoms bonded to an alkyl moiety containing 1 to about 10 carbon atoms;
(3) optionally substituted heteroaralkyl containing a heteroaryl moiety having 5 to about 10 ring atoms bonded to an alkyl moiety having 1 to about 10 carbon atoms;
(4) optionally substituted carbocycloalkyl containing a carbocyclic moiety having 3 to about 10 ring carbon atoms bonded to an alkyl moiety having 1 to about 10 carbon atoms;
(5) optionally substituted heterocycloalkyl containing a heterocyclic moiety having 3 to about 10 ring atoms bonded to an alkyl moiety having 1 to about 10 carbon atoms;
(6) optionally substituted alkenyl having 2 to about 10 carbon atoms;
(7) optionally substituted aralkenyl containing an aryl moiety having 5 to about 10 ring atoms bonded to an alkenyl moiety having 2 to about 10 carbon atoms;
(8) optionally substituted heteroaralkenyl containing a heteroaryl moiety having 5 to about 10 ring atoms bonded to an alkenyl moiety having 2 to about 10 carbon atoms;
(9) optionally substituted carbocycloalkenyl containing a carbocyclic moiety having 3 to about 10 ring carbon atoms bonded to an alkenyl moiety having 2 to about 10 carbon atoms;
(10) optionally substituted heterocycloalkenyl containing a heterocyclic moiety having 3 to about 10 ring atoms bonded to an alkenyl moiety having 2 to about 10 carbon atoms;
(11) optionally substituted aryl having 6 to about 10 ring carbon atoms;

(12) optionally substituted heteroaryl having 5 to about 10 ring atoms with ring atoms selected from carbon atoms and heteroatoms, where the heteroatoms are nitrogen, oxygen or sulfur;

(13) optionally substituted carbocyclic having 3 to about 10 ring carbon atoms;

or

(14) optionally substituted heterocyclic having 3 to about 10 ring atoms with ring atoms selected from carbon atoms and heteroatoms, where the heteroatoms are nitrogen, oxygen or sulfur;

In one embodiment, Q is phenyl optionally substituted with 1–5, 2–4, or 2–3 substituents selected from halo, nitro, $C_1$–$C_6$ alkyl, $C_2$–$C_6$ alkenyl, $C_2$–$C_6$ alkynyl, $NR_7R_8$, $OR_7$, $SR_7$, $C_1$–$C_6$ alkyl-C(O)$OR_7$, $OC_1$–$C_6$ alkyl-C(O)$OR_7$, $C_1$–$C_6$ alkyl-$OR_7$, $OC_1$–$C_6$ alkyl-$OR_7$, $C_1$–$C_6$ alkyl-$NR_7R_8$, $OC_1$–$C_6$ alkyl-$NR_7R_8$, $C_1$–$C_6$ alkyl-C(O)$NR_7R_8$, $OC_1$–$C_6$ alkyl-C(O)$NR_7R_8$, $C_1$–$C_6$ alkyl-C(O)$R_7$, $OC_1$–$C_6$ alkyl-C(O)$R_7$, $C_1$–$C_6$ haloalkyl, O-aralkyl (e.g. benzyloxy), C(O)$OR_7$, C(O)$NR_7R_8$, OC(O)$NR_7R_8$, NHC(O)$R_7$, NHC(O)$NR_7R_8$, $NR_7S(O)_nR_1$, $NR_7S(O)_nR_7$, $S(O)_nR_7$, $S(O)_nNR_7$, where $R_7$ and $R_8$ independently are H or $C_1$–$C_6$ alkyl. In this embodiment, each of the remaining variables $R_2$, $R_5$, $R_6$, A, B, and $R_1$ may be independently selected to have any of the definitions described above. Each alkyl, alkenyl and alkynyl moiety may also be substituted as defined above.

In one embodiment, Q has the structure

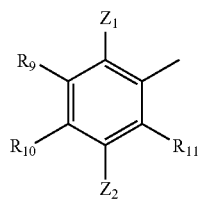

wherein $R_9$ is H, $C_1$–$C_6$ alkyl, $C_2$–$C_6$ alkenyl, $C_2$–$C_6$ alkynyl, $C_1$–$C_6$ alkoxy, hydroxy, $NR_7R_8$, $SR_7$ or $OR_7$, where $R_7$ and $R_8$, independently, are H or unsubstituted or substituted $C_1$–$C_6$ alkyl;

$R_{10}$, $R_{11}$ and $Z_2$, independently, are each selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-C(O)$R_7$, $C_1$–$C_6$ alkyl-C(O)$NR_7R_8$, $C_1$–$C_6$ alkyl-C(O)$OR_7$, $C_1$–$C_6$ alkyl-OC(O)$R_7$, $C_1$–$C_6$ alkyl-$OR_7$, $OC_1$–$C_6$ alkyl-C(O)$R_7$, $OC_1$–$C_6$ alkyl-C(O)$OR_7$, $OC_1$–$C_6$ alkyl-OC(O)$R_7$, O—$C_1$–$C_6$ alkyl-$OR_7$, $OC_1$–$C_6$ alkyl-C(O)$NR_7R_8$, $C_1$–$C_6$ haloalkyl, $OR_{12}$, $C_1$–$C_6$ alkyl-$R_{12}$, $OC_1$–$C_6$ alkyl-$R_{12}$, C(O)$OR_7$, C(O)$OR_{12}$, C(O)$NR_7R_8$, OC(O)$NR_7R_8$, $NR_7C(O)R_7$, $NR_7C(O)R_{12}$, $NR_7C(O)$—$NR_7R_8$, $NR_7$—($C_1$–$C_6$ alkyl)-C(O)—$NR_7R_8$, $NR_7C(O)OR_7$, $NR_7C(O)OR_{12}$, $NR_7S(O)n$-$R_1$, $NR_7S(O)n$-$R_7$ and $NR_7S(O)n$-$R_{12}$, where $R_7$ and $R_8$, independently, are H or unsubstituted or substituted $C_1$–$C_6$ alkyl, $R_{12}$ is unsubstituted or substituted $C_6$–$C_{10}$ aryl or heterocycle as defined above and n is 1 or 2;

$Z_1$ is H, $C_1$–$C_6$ alkyl, $C_1$–$C_6$ alkoxy, halogen or nitro. In this embodiment, each of the remaining variables $R_2$, $R_5$, $R_6$, A, B, X, and Y may be independently selected to have any of the definitions described above. Each alkyl, alkenyl and alkynyl moiety may also be substituted as defined above.

In various aspects of the invention, $Z_1$ and $Z_2$ may be hydrogen; $Z_1$, $Z_2$ and $R_{11}$ may be hydrogen; or $Z_1$, $R_{10}$ and $R_{11}$ may be hydrogen; and the remaining ring substituents are as defined above.

In another embodiment, the substituents at the 4- and 5-positions or at the 5- and 6-positions of the ring when Q is substituted phenyl may be bonded together to form an unsubstituted or substituted carbocyclic or hetercyclic ring. Examples of such compounds are shown below, where the symbol

includes a 5-membered or a 6-membered carbocyclic or heterocyclic ring which is fused to the phenyl ring in the positions shown below as represented by formula IIa and IIb.

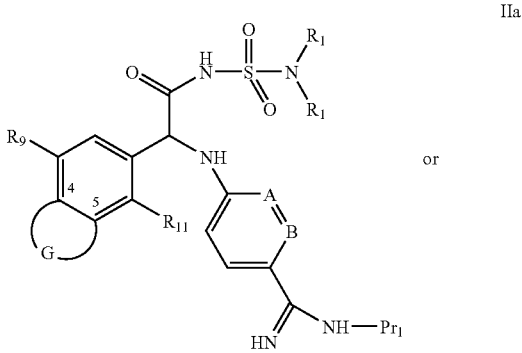

Examples of suitable 5-membered or a 6-membered carbocyclic or heterocyclic rings which may be fused to the phenyl ring include the ring systems shown below, where $R_6$ is as defined above.

-continued

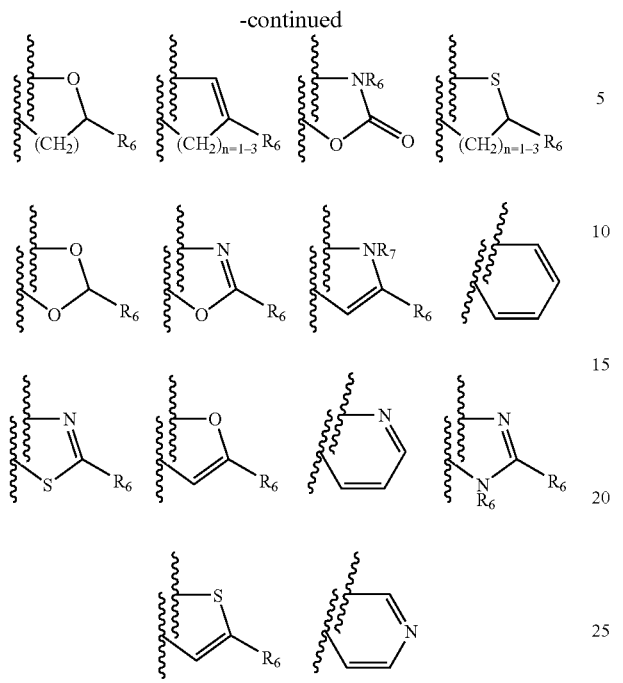

Compounds in which Q is substituted phenyl and $R_{10}$ is selected from the group consisting of $C_1$–$C_6$ alkyl, $C_1$–$C_6$ alkoxy, $C_1$–$C_6$ aminoalkyl, $C_1$–$C_6$ haloalkyl, $C_1$–$C_6$ hydroxyalkyl, phenyl, phenoxy, benzyl, benzyloxy, as well as phenoxy- and benzyloxy-substituted with $C_1$–$C_6$ alkyl, $C_1$–$C_6$ alkoxy, halo, $C_1$–$C_6$ haloalkyl, $C_1$–$C_6$ hydroxyalkyl, $C_1$–$C_6$ aminoalkyl, OC(O)—$C_1$–$C_6$ alkyl, C(O)O—$C_1$–$C_6$ alkyl and C(O)OH, where each of the remaining variables may be independently selected to have any of the definitions described above.

Also of interest are compounds in which $R_{11}$ is $NR_7C_1$–$C_6$ alkyl-C(O)$NR_7R_8$, $NR_7S(O)n$-$R_7$ or N $R_7S(O)n$-$R_{12}$, n is 1 or 2 and/or where $Z_1$=$Z_2$=H and/or where $R_{10}$ is $OR_7$, $OR_{12}$, $OC_7$–$C_{10}$-aralkyl, $OC_1$–$C_6$ alkyl-$OR_7$ or $OC_1$–$C_6$ alkyl-$OR_{12}$ where $R_7$ and $R_{12}$ are unsubstituted or substituted as defined above. Suitable substituted $R_7$ and $R_{12}$ include these groups substituted as described above, for example, having 1 or 2 $C_1$–$C_6$ alkoxy, $C_1$–$C_6$ alkoxy-$C_1$–$C_6$ alkoxy, halo, $C_1$–$C_6$ haloalkyl, $C_1$–$C_6$ hydroxyalkyl, $C_1$–$C_6$ aminoalkyl, OC(O)—$C_1$–$C_6$ alkyl, C(O)O—$C_1$–$C_6$ alkyl, $C_1$–$C_6$ alkyl C(O)$OR_7$, $C_1$–$C_6$ alkyl OC(O)$R_7$ or C(O)OH. In these compounds, each of the remaining variables may be independently selected to have any of the definitions described above.

In another embodiment, A and B are independently CH or $CR_3$, where $R_3$ is H, halogen, $C_{1-6}$ alkyl or OH, where the remaining variables may be independently selected to have any of the definitions described above. In one embodiment, one of A and B is F while the other is C—F. In another embodiment, both A and B are CH.

In another embodiment, $R_6$ is H or $R_3$ is CH, where the remaining variables may be independently selected to have any of the definitions described above.

In particular embodiments, compounds of formula I are selected from the group consisting of the compounds in Table 1.

TABLE 1

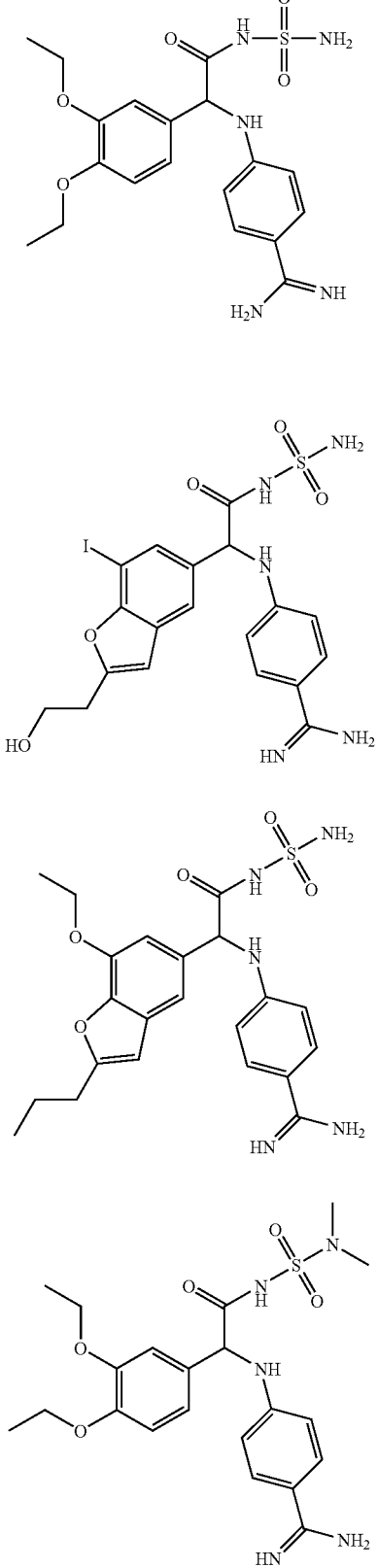

TABLE 1-continued
5
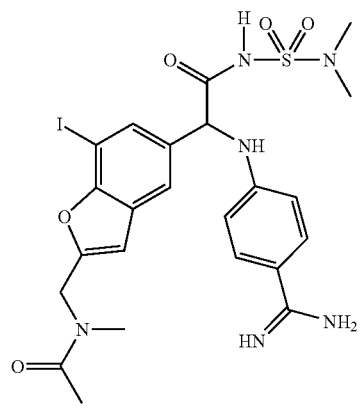
6
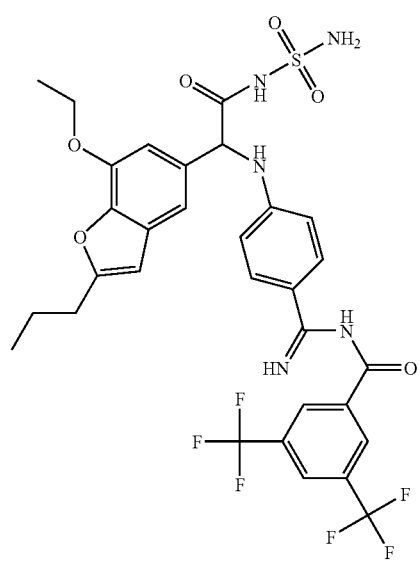
7
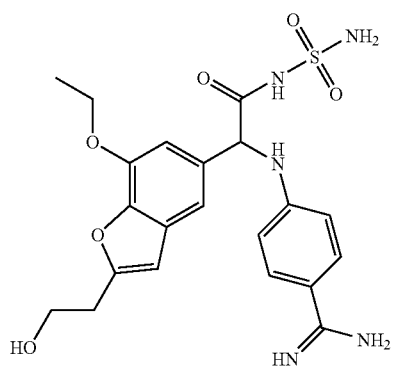
TABLE 1-continued
8
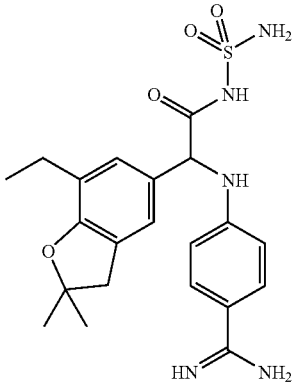
9
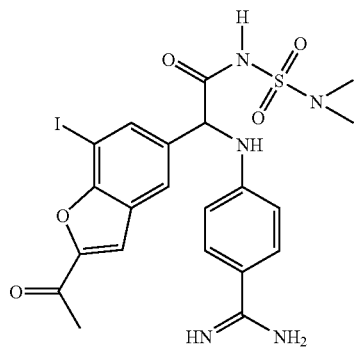
10
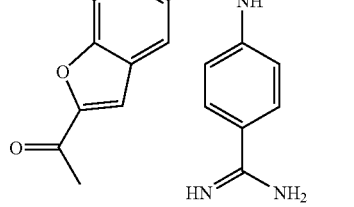
11
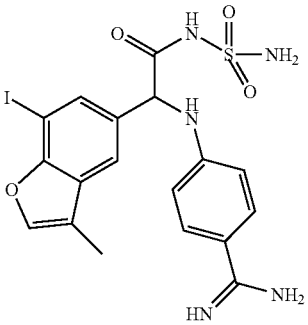

TABLE 1-continued
| 12 | 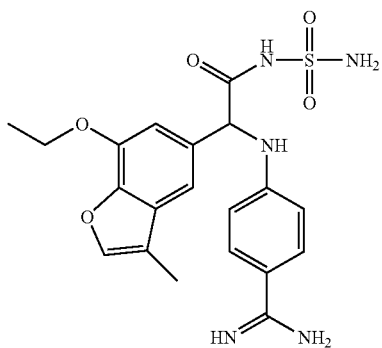 |
| 13 | 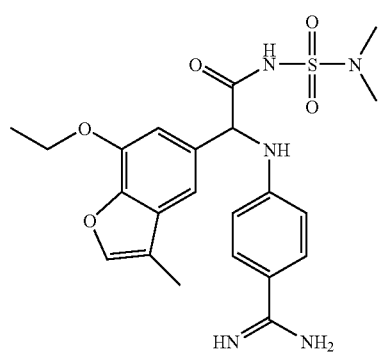 |
| 14 | 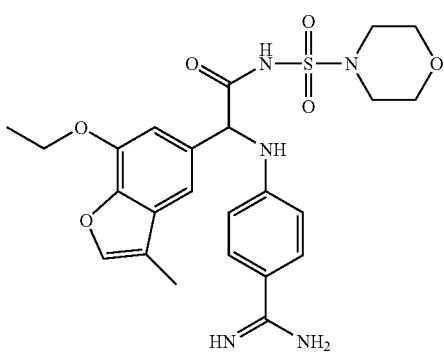 |
| 15 | 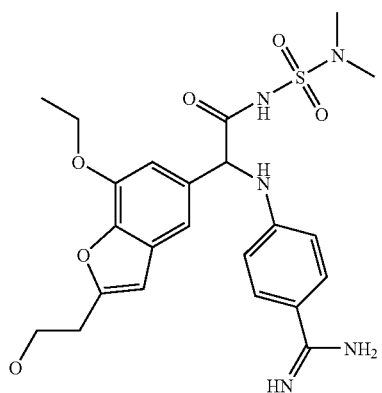 |
TABLE 1-continued
| 16 | 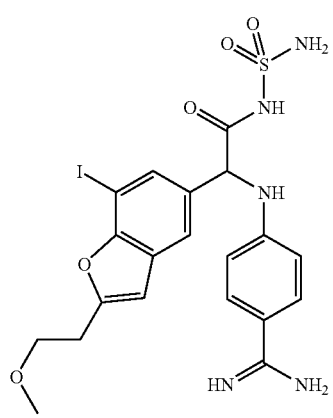 |
| 17 | 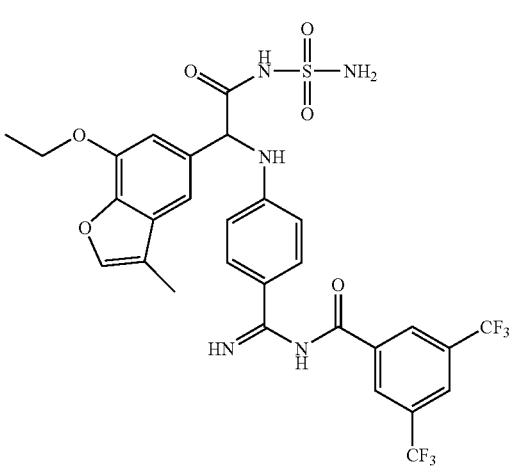 |
| 18 | 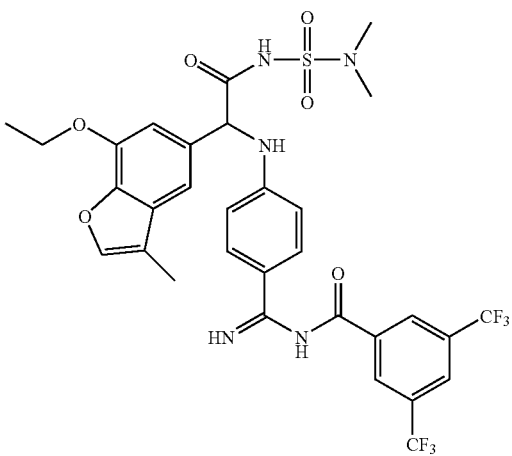 |

TABLE 1-continued
| 19 | 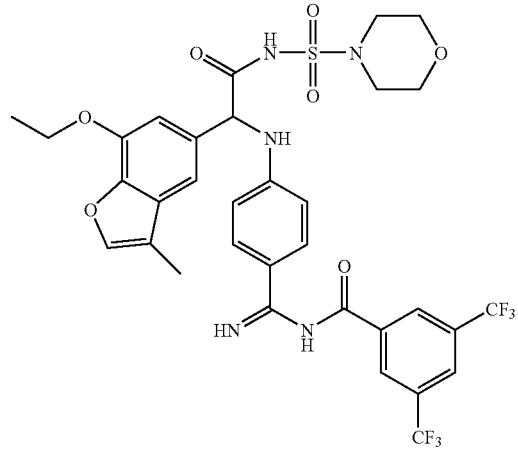 |
|---|---|
| 20 | 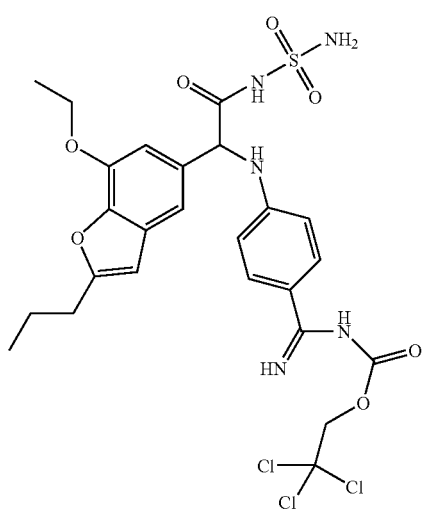 |
| 21 | 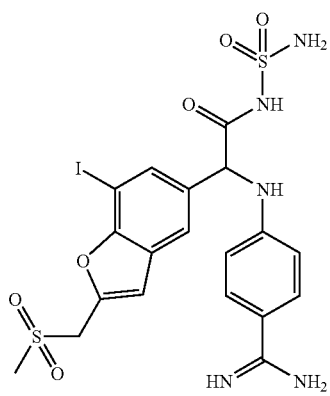 |
TABLE 1-continued
| 22 | 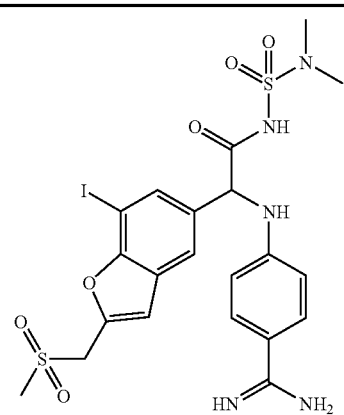 |
|---|---|
| 23 | 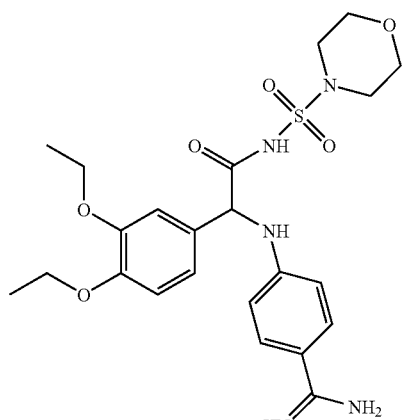 |
| 24 | 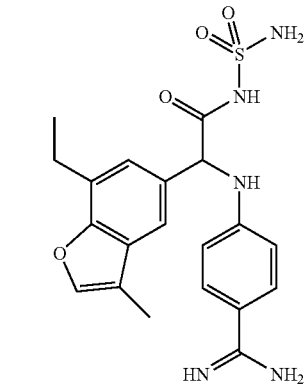 |
| 25 | 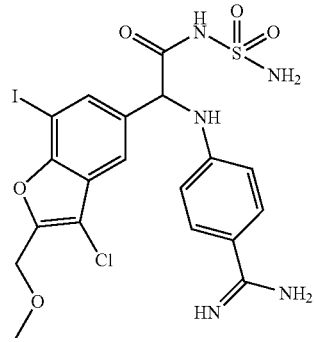 |

TABLE 1-continued
26 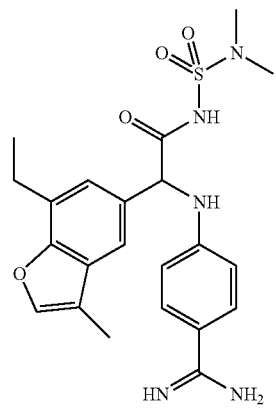
27 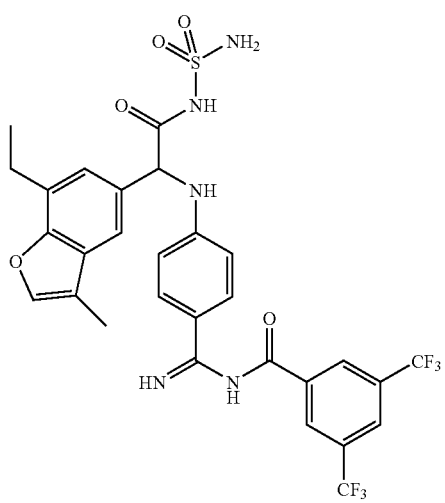
28 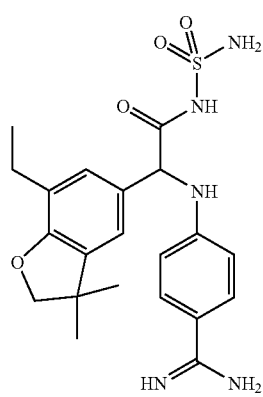
TABLE 1-continued
29 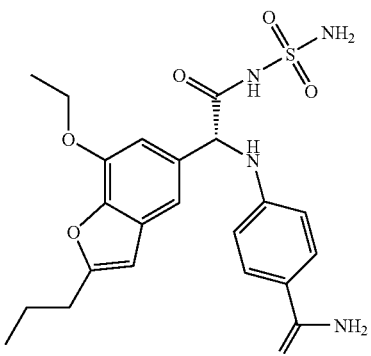
30 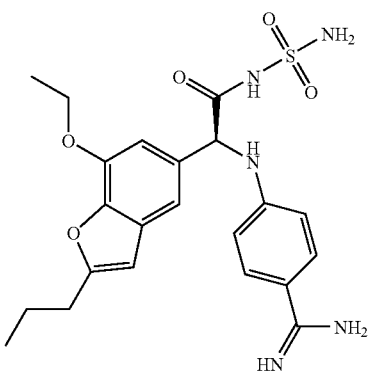
31 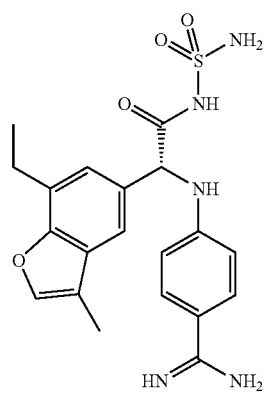
32 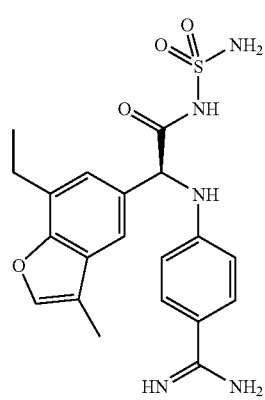

TABLE 1-continued
| 33 | 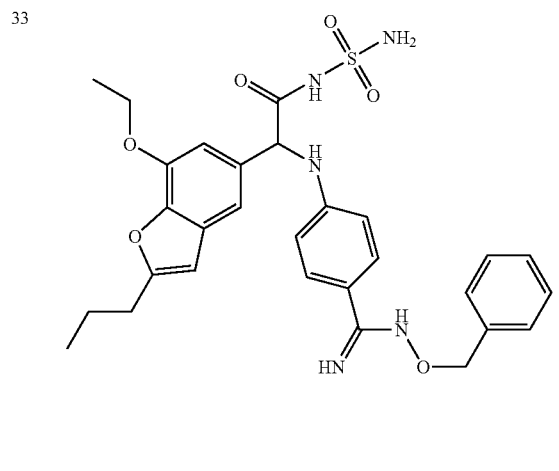 |
| --- | --- |
| 34 | 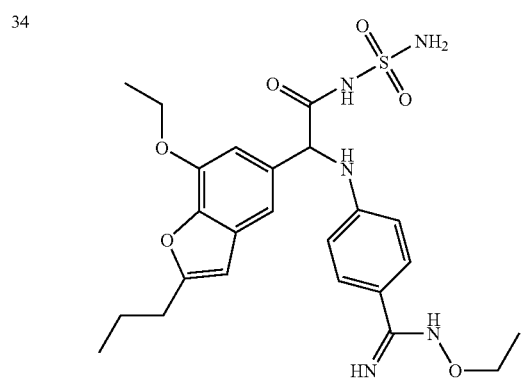 |
| 35 | 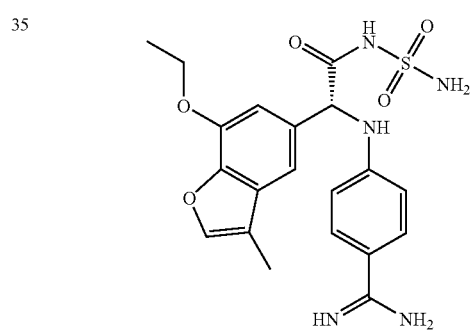 |
| 36 | 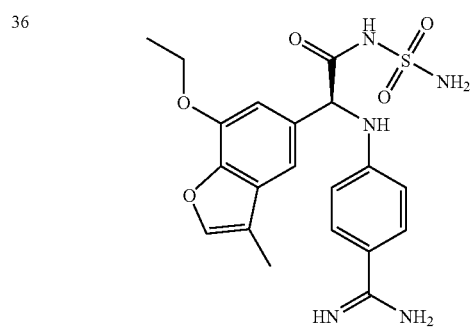 |
TABLE 1-continued
| 37 | 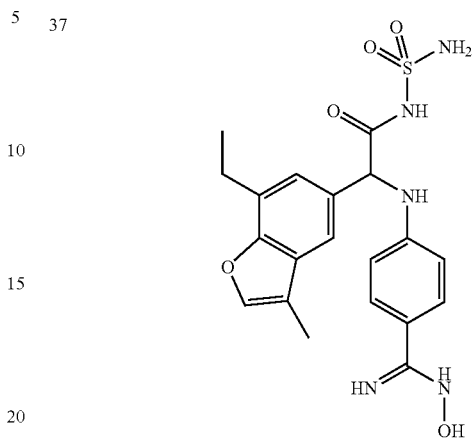 |
| --- | --- |
| 38 | 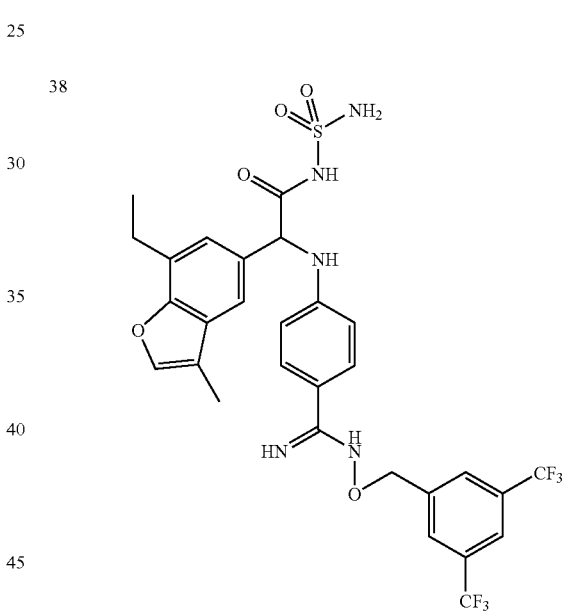 |
| 39 | 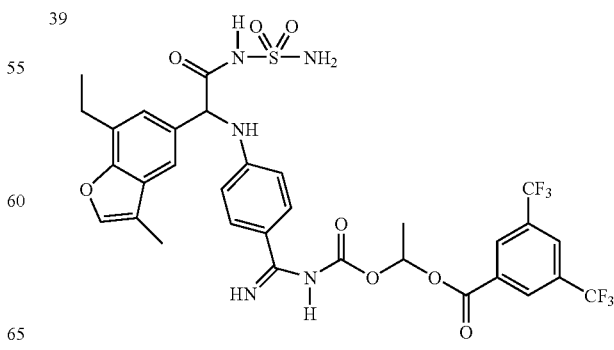 |

TABLE 1-continued
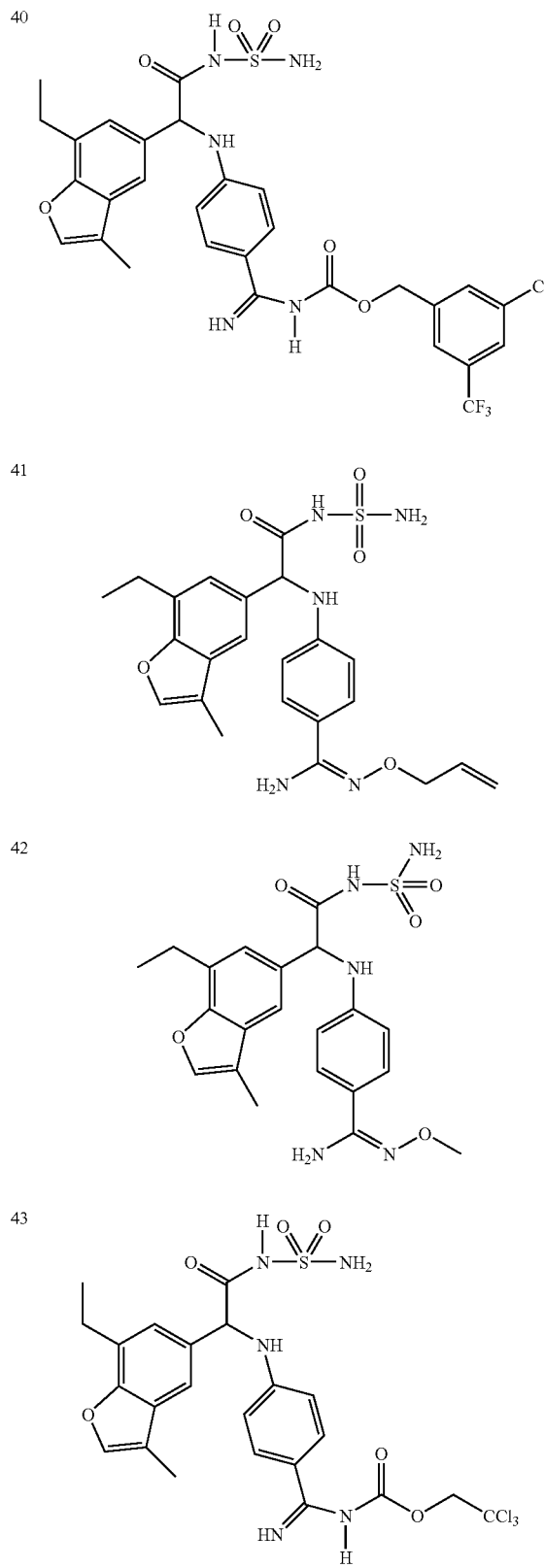
TABLE 1-continued
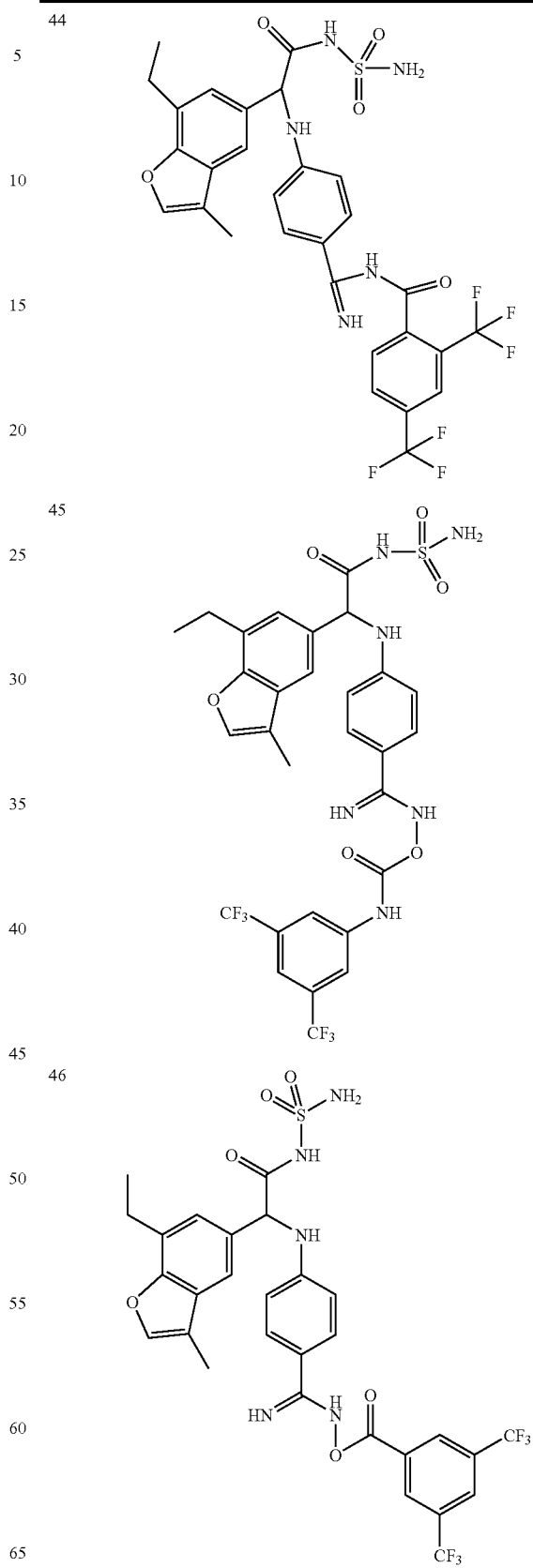

TABLE 1-continued

47

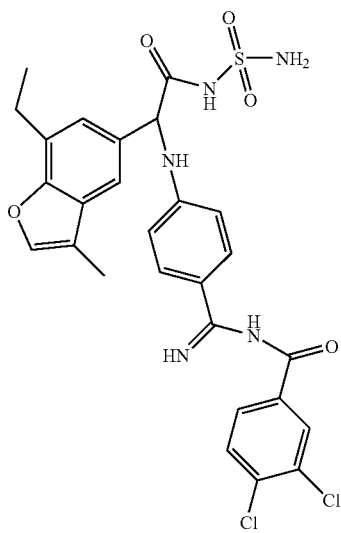

48

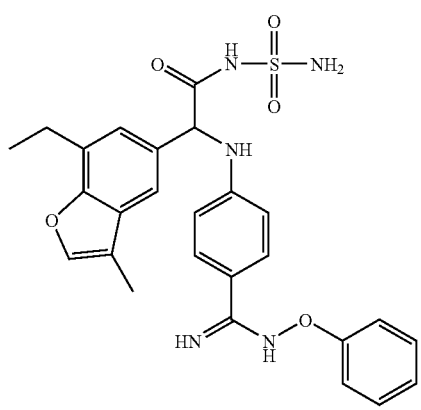

An exemplary reaction in the synthesis of compounds of the invention involves reacting a carboxylic acid intermediate with a sulfamide $NH_2$—$SO_2$—$NR_1R_1$ as shown below

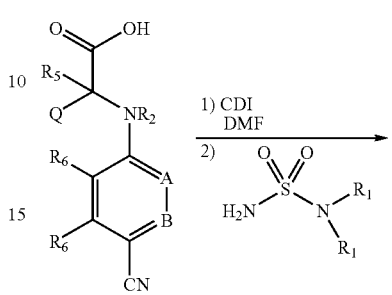

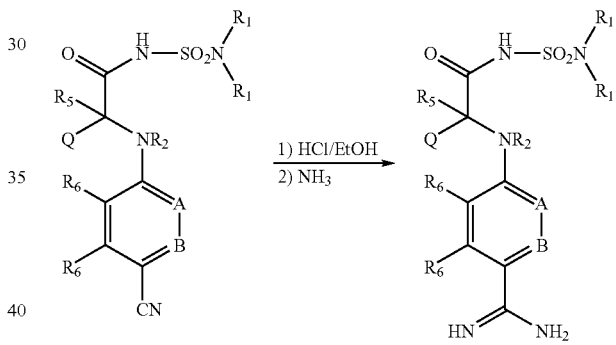

in which A, B, $R_2$, $R_5$, $R_6$, and Q have the meanings described above. The cyano group of the resulting acyl sulfamide compound is converted to the active compound incorporating an amidino group $C(NH)NH_2$ using known procedures. For example, the cyano compound may be reacted with hydroxylamine ($NH_2OH$, or a salt thereof), in a solvent such as an alcohol, followed by reduction with Raney Ni, in a solvent such as an alcohol, or may be reacted by the method of Pinner, first with ethanolic HCl and then with alcoholic ammonia to yield the corresponding amidino compounds. Alternatively, a modified Pinner reaction using pyridine/diethylamine (1/1)/hydrogen sulfide followed by methyl iodide/acetonitrile and then ammonium acetate/ethanol will provide the desired amidino compound.

The carboxylic acid compound above may be prepared using standard synthetic techniques such as those described in U.S. Pat. No. 6,472,393, the entirety of which is incorporated herein by reference. One such synthetic route is a condensation reaction using appropriately substituted precursors as shown in the scheme below.

Synthesis of the Acylsulfamide Compounds

Compounds of the present invention can be prepared by methods employing standard chemical methodologies described and referenced in standard textbooks (e.g. Smith, M. and March, J. "March's Advanced Organic Chemistry: Reactions, Mechanisms, and Structure, 5th Edition" McGraw-Hill, New York, 2001); Collman, J. P., Hegedus, L. S., Norton, J. R., Finke, R. G. "Principles and Applications of Organotransition Metal Chemistry" University Science, Mill Valley, 1987; Larock, R. C. "Comprehensive Organic Transformations" Verlag, New York, 1989). Reagents for the transformations elucidated in the embodiments of the invention are standard and may be found in standard reference books and series such as "Fiesers' Reagents for Organic Synthesis" Volumes 1–22 (John Wiley, New York).

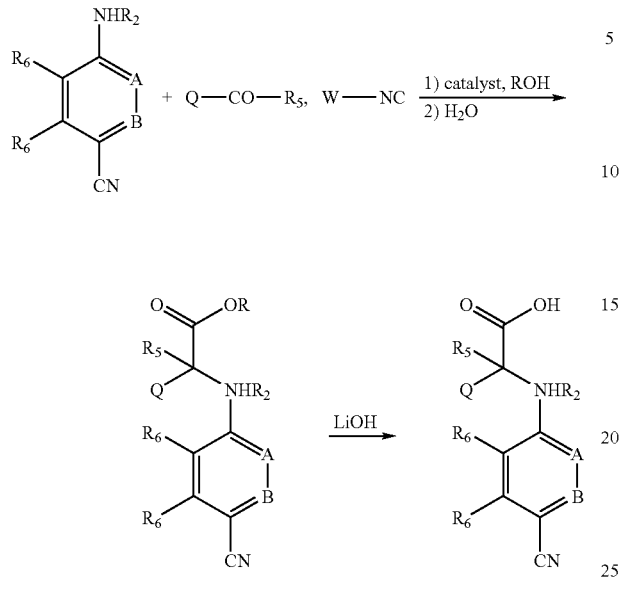

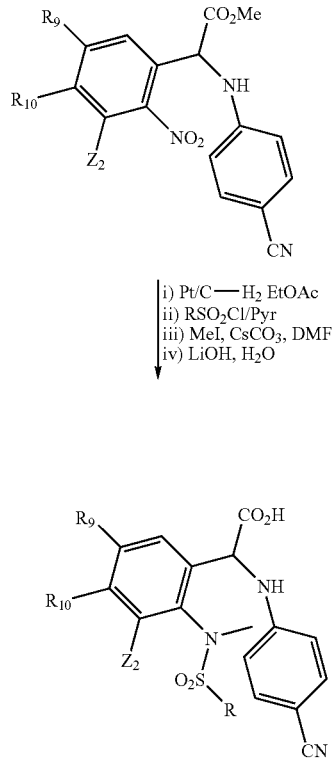

i) Pt/C—H$_2$ EtOAc
ii) RSO$_2$Cl/Pyr
iii) MeI, CsCO$_3$, DMF
iv) LiOH, H$_2$O

This condensation is performed in the presence of a catalyst, such as a Lewis acid catalyst, and an alkyl alcohol (ROH), such as a lower, i.e. $C_1$–$C_6$, alkyl alcohol like methanol, ethanol, i-propanol, etc., followed by hydrolysis of the intermediate, with an excess of water, generally about 10 or more equivalents of water. Suitable Lewis Acids include BF$_3$ etherate, AlCl$_3$, etc. W—NC is an isonitrile in which W may be any suitable hydrocarbon group, generally an alkyl, carbocycloalkyl, or aralkyl group, for example having no more than about 12 carbon atoms. One exemplary isonitrile is benzyl isonitrile. The ester product may be purified by standard techniques, including high pressure liquid chromatography (HPLC), column chromatography, recrystallization, etc. Conversion of the ester to the carboxylic acid intermediate is easily performed by saponification with an alkali-metal hydroxide such as lithium, sodium, or potassium hydroxide. The carboxylic acid intermediate in turn may be reacted with the desired sulfamide followed by conversion of the cyano group to amidine to give the active compound of the invention.

In a particular example, a carboxy intermediate which incorporates a sulfonamide group at $R_{11}$ may be prepared using the following scheme.

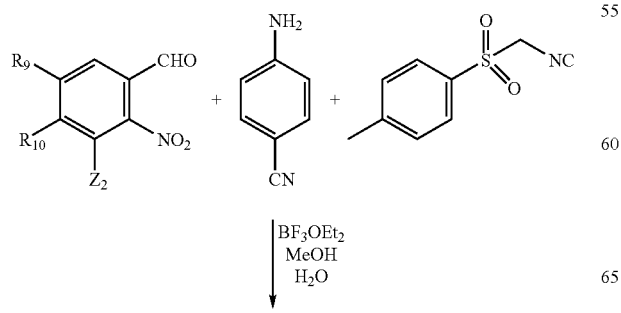

In another variation of this embodiment, Q is a substituted phenyl having substituents $Z_1$, $Z_2$, and $R_9$–$R_{11}$ as described below.

When the corresponding compounds in which A and B are nitrogen are desired, the aniline or substituted aniline used in the reactions described above is replaced with the corresponding amino-pyridine or substituted amino-pyridine compounds.

Compounds in which a sulfonamide nitrogen bears a substituent can be prepared by conventional alkylation of the nitrogen atom using known reactions, for example, alkylation with dialkyl sulfate, alkyl halide etc, according to known procedures.

In one embodiment, Q is a substituted aryl, such as a substituted phenyl group with the structure shown below.

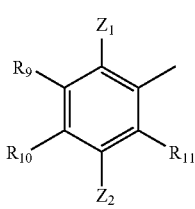

In this structure, $Z_1$, $Z_2$, $R_9$–$R_{11}$ are as defined above both generally and in exemplary embodiments. Compounds of this embodiment are prepared as described in scheme 1 above using an appropriately substituted benzaldehyde having structure Q-CHO ($R_5$ is H). These substituted benzaldehydes are readily available from commercial sources or can be easily prepared from available benzaldehydes using established synthetic chemistry techniques.

In one embodiment, Q is substituted with a nitro group. One position for the nitro group is at $R_{11}$ (where $Z_1$, $Z_2$, $R_9$ and $R_{10}$ are as defined above generally and in exemplary embodiments), which nitro group can be further reduced to an amino group using a suitable reducing agent. Generally, the cyano-amine compound or the cyano-sulfonamide compound shown in a previous scheme will be reacted with a reducing agent which will preferentially reduce the nitro group at $R_{11}$ over the cyano group. Any reducing agent having these properties may be used, for example, hydrogen and a Pt/C catalyst. The aniline resulting from the reduction can then be reacted with a sulfonyl chloride ($ClSO_2W$ where W is as defined above) to produce a sulfonamide compound.

Other compounds of the invention, including heterocyclic compounds, are readily prepared from simple starting materials which can be used in the synthetic schemes described above. For example, beginning with simple nitro and hydroxy substituted aldehydes, condensation as described above provides the corresponding esters which can be converted directly to cyclic urethane or oxazole compounds which can then be further elaborated as already described to provide compounds of the invention. These reactions are shown schematically below for rings fused in the 5-position and 6-position.

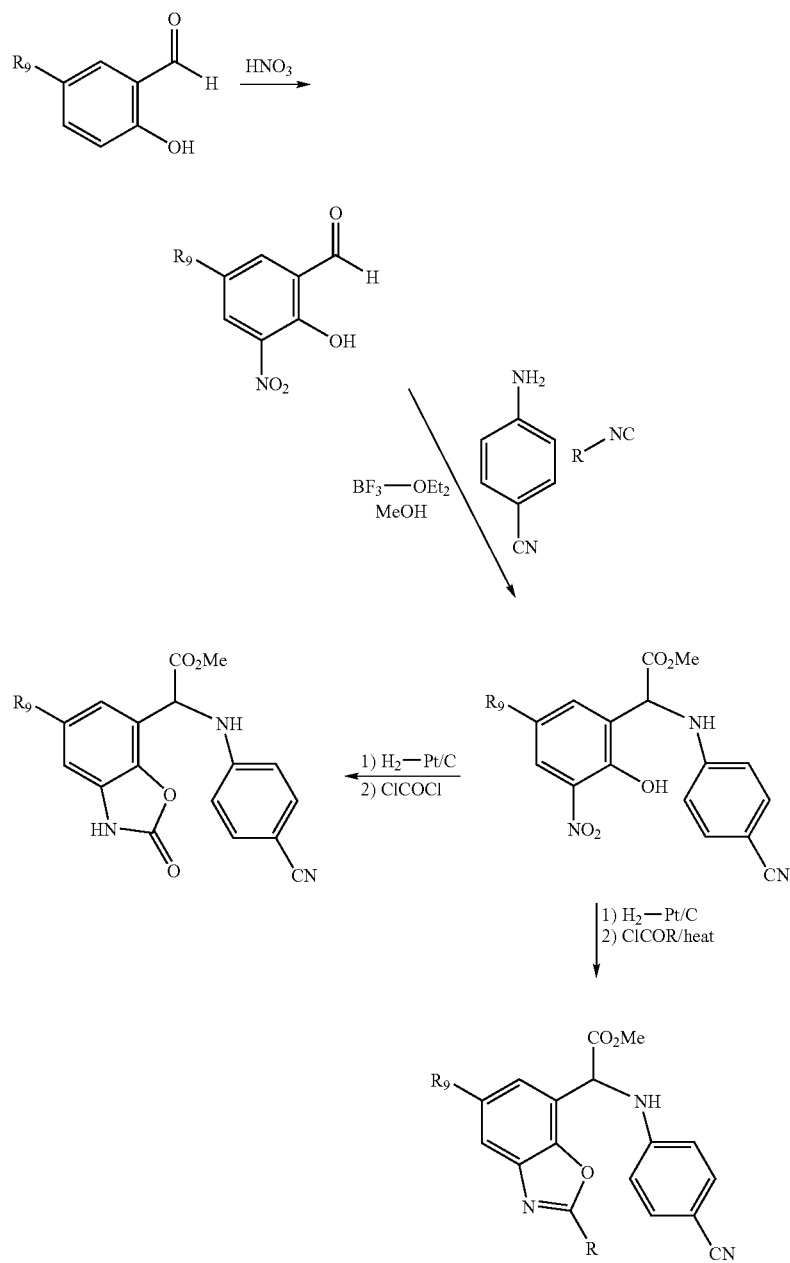

Compounds in which the ring is fused to the 4-position and the 5-position of the phenyl ring are prepared by analogous methods stating with the appropriately substituted aldehyde as shown below.

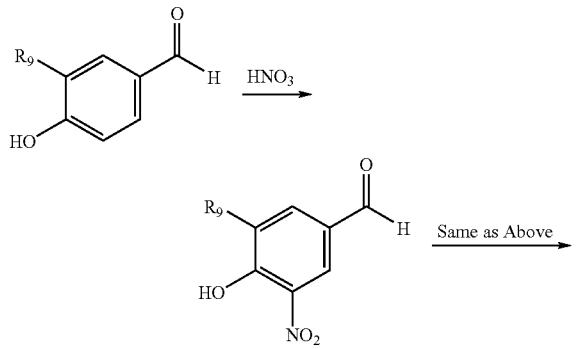

Other fused heterocyclic compounds are prepared using conventional synthetic chemical reactions and appropriately substituted starting materials which are well known in the art of chemical synthesis to provide additional compounds of the invention. For example, fused furan ring systems can be prepared from the corresponding halo and hydroxy substituted aldehydes as shown below.

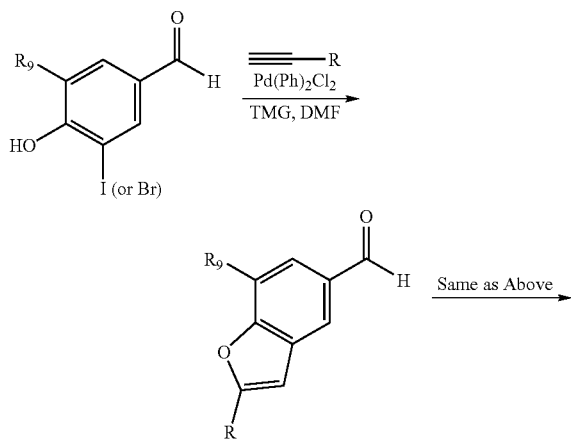

Also included in the scope of this invention are prodrugs of the compounds described above. Suitable prodrugs include known amino-protecting and carboxy-protecting groups which are released, for example hydrolyzed, to yield the parent compound under physiologic conditions. An exemplary class of prodrugs are compounds in which a nitrogen atom in an amino, amidino, aminoalkyleneamino, iminoalkyleneamino or guanidino group is substituted with a hydroxy (OH) group, an alkylcarbonyl (—CO—W) group, an alkoxycarbonyl (—CO—OW), an acyloxyalkyl-alkoxycarbonyl (—CO—O—W—O—CO—W) group where W is a monovalent or divalent group and as defined above or a group having the formula —C(O)—O—CP1P2-haloalkyl, where P1 and P2 are the same or different and are H, $C_1$–$C_6$ alkyl, $C_1$–$C_6$ alkoxy, cyano, $C_1$–$C_6$ haloalkyl or aryl. The nitrogen atom may be one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in WO98/46576, published 22 Oct. 1998.

The compounds of the invention contain one or more asymmetric carbon atoms. Accordingly, the compounds may exist as diastereomers, enantiomers or mixtures thereof. The syntheses described above may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

Activity

It has been discovered that the compounds of the invention when made and selected as disclosed herein are inhibitors of serine protease enzymes, for example, factor VIIa, TF/factor VIIa, factor Xa, kallikrein and/or thrombin. These compounds are capable of inhibiting the catalytic activity of these enzymes and as such function to inhibit the coagulation cascade and prevent or limit coagulation and/or the formation of thrombi or emboli in blood vessels and/or increase the time of coagulation of blood. The compounds of the present invention, therefore, inhibit the ability of TF/factor VIIa to convert factor X to factor Xa, inhibit the ability of factor Xa to convert prothrombin to thrombin (factor IIa); and/or the ability of thrombin to convert fibrinogen to fibrin monomers.

The anti-coagulant activity of the compounds of the invention can be tested using assays. Prothrombin time (PT) and activated partial thromboplastin time (APTT) clotting time assays can be performed in pooled normal plasmas (human or various animal species) following addition of increasing concentrations of inhibitors to the plasma. Clotting times are determined using an ACL 300 Automated Coagulation Analyzer (Coulter Corp., Miami, Fla.) and commercially available reagents as follows.

PT assay: Aqueous solutions of inhibitor at various concentrations are added to pooled normal plasma in a ratio of 1 part inhibitor to 9 parts plasma. These mixtures are then added to the analyzer's sample cups. Innovin® (Dade International Inc., Miami, Fla.), a mixture of human relipidated tissue factor and $Ca^{++}$ ions is added to the reagent cup. Precise volumes of sample and Innovin® are automatically transferred to cells of an acrylic rotor that is pre-equilibrated to 37° C. Following a 2 minute incubation period, coagulation is initiated when the two components are mixed together by centrifugation. Coagulation is monitored optically and clotting time is reported in seconds. In agreement with Janson et al. (Janson, T. L. et al (1984) Haemostasis 14:440–444) relipidated human tissue factor is a potent initiator of coagulation in all species tested. In this system, the clotting time of control plasmas (plasma plus inhibitor diluent) is typically 8 to 10 seconds. A curve is fit to the clotting time versus inhibitor concentration data and the concentration at which the PT is doubled compared to control plasma is determined for each inhibitor.

APTT assay: Inhibitor and plasma are mixed together and transferred to the ACL 300 sample cups as described above. Actin FS® and $CaCl_2$ (Dade International Inc., Miami, Fla.), are added to reagent cups 1 and 2 respectively. Precise volumes of sample and activator (Actin FS®) are automatically transferred to cells of a pre-equilibrated rotor (37C) and mixed by centrifugation. Following a 2 minute activation period, coagulation is initiated by the addition of $CaCl_2$. Coagulation is monitored and data calculated as described in the PT method. APTT of plasma controls is typically 12 to 32 seconds, depending on the species of plasma used in the assay.

The compounds of the invention are useful as diagnostic reagents in vitro for inhibiting clotting in blood drawing tubes. The use of stoppered test tubes having a vacuum therein as a means to draw blood is well known (Kasten, B. L., (1990) "Specimen Collection", Laboratory Test Handbook, 2nd Ed., Lexi-Comp Inc., Cleveland, PP 16–17, Eds. Jacobs, D. S. et al). Such vacuum tubes may be free of clot-inhibiting additives, in which case, they are useful for the isolation of mammalian serum from the blood. They may also contain clot-inhibiting additives, such as heparin salts, citrate salts or oxalate salts, in which case they are useful for the isolation of mammalian plasma from the blood. The compounds of the invention may be incorporated into blood collection tubes and function to inhibit TF/factor VIIa, factor Xa, thrombin and/or kallikrein and to prevent clotting of the mammalian blood drawn into the tubes.

When used in blood collection tubes, the compounds of the invention may be used alone, as mixtures or in combination with other clotting inhibiting compounds known in this art. The amount of the compound of the invention should be an amount sufficient to prevent or inhibit the formation of a clot when blood is drawn into the tube. These compounds may be introduced into the tubes in the same manner as known clot-inhibiting compounds such as heparin salts. Liquids are usually lyophilized using known methods. Typically, the tubes will contain about 2 to about 10 ml of mammalian blood and the compounds are added in an amount sufficient to prevent coagulation of this amount of blood. A suitable concentration is about 10–1000 nM.

These compounds also inhibit the formation of emboli and thrombi in the circulatory system in mammals and therefore are useful in vivo. Thromboembolic disorders have been shown to be directly related to the susceptibility of the mammal to formation of emboli and thrombi. For example, the formation of a thrombus in a veinous vessel results in thrombophlebitis, which is typically treated with rest and the administration of anticoagulants. Other conditions which can be treated with the anticoagulant compounds of the invention include, thrombolymphangitis, thrombosinusitis, thromboendocarditis, thromboangiitis, and thromboarteritis.

Mammals exposed to medical procedures such as angioplasty and thrombolytic therapy are particularly susceptible to thrombus formation. The compounds of the present invention can be used to inhibit thrombus formation following angioplasty. They may also be used in combination with antithrombolytic agents such as tissue plasminogen activator and its derivatives (U.S. Pat. Nos. 4,752,603; 4,766,075; 4,777,043; EP 199 574; EP 238 304; EP 228 862; EP 297 860; WO 89/04368; WO 89/00197), streptokinase and its derivatives, or urokinase and its derivatives to prevent arterial reocclusion following thrombolytic therapy. When used in combination with the above thrombolytic agents, the compounds of the present invention may be administered prior to, simultaneously with, or subsequent to the anti-thrombolytic agent.

Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders.

Thus, the compounds described herein may be useful in treating thromboembolic disorders in mammals. The compounds described herein may also be used as adjuncts to anticoagulant therapy, for example in combination with aspirin, heparin or warfarin and other anticoagulant agents. The various coagulation disorders described above are treated with the compounds of the invention in such a fashion as to prevent bleeding as a result of the disorder. The application of the compounds described herein for these and related disorders will be apparent to those skilled in the art.

Compounds of this invention are also useful as intermediates generally, or as precursors of coagulation serine protease inhibitors and thus in addition to treating cardiovascular disease, these compounds may be usefully employed in metastatic disease, or for any disease where inhibition of coagulation is indicated.

Administration of Acylsulfamide Compounds

The acylsulfamide compounds of the invention may be administered by any route appropriate to the condition to be treated. Suitable routes include oral, parenteral (including subcutaneous, intramuscular, intravenous, intradermal, intrathecal and epidural), rectal, nasal, topical (including buccal and sublingual), vaginal and the like. It will be appreciated that the preferred route may vary with for example the condition of the recipient. Where the acylsulfamide compound is administered orally, it may be formulated as a pill, capsule, tablet, etc. with a pharmaceutically acceptable carrier or excipient. Where the acylsulfamide compound is administered parenterally, it may be formulated with a pharmaceutically acceptable parenteral vehicle and in a unit dosage injectable form.

Pharmaceutical Formulations of Acylsulfamide Compounds

Pharmaceutical, formulations of therapeutic acylsulfamide compounds of the invention may be prepared for various routes and types of administration. An acylsulfamide compound having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01–100 mg/kg, namely about 0.1 to 20 mg/kg of patient body weight per day, with the typical initial range of compound used being 0.3 to 15 mg/kg/day.

The acylsulfamide compound of the invention is administered by any suitable means, including oral, topical, transdermal, parenteral, subcutaneous, intraperitoneal, intrapulmonary, and intranasal, and, if desired for local immunosuppressive treatment, intralesional administration (including perfusing or otherwise contacting the graft with the inhibitor before transplantation). Parenteral infusions include intramuscular, intravenous, intraarterial, intraperitoneal, or subcutaneous administration.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate)microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the acylsulfamide compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of an acylsulfamide compound may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

Although oral administration of protein therapeutics are disfavored due to hydrolysis or denaturation in the gut, formulations of acylsulfamide compound suitable for oral administration may be prepared as discrete units such as capsules, cachets or tablets each containing a predetermined amount of the acylsulfamide compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of an acylsulfamide compound intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

An acylsulfamide compound of the invention may be combined in a pharmaceutical combination formulation, or dosing regimen as combination therapy, with a second compound having anticoagulant properties or is useful for treating thromboembolic disorders. The second compound of the pharmaceutical combination formulation or dosing regimen preferably has complementary activities to the acylsulfamide compound of the combination such that they do not adversely affect each other. Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Acyl Sulfamide Compounds

Also falling within the scope of this invention are the in vivo metabolic products of the acylsulfamide compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $C^{14}$ or $H^3$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the acylsulfamide compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an acylsulfamide compound or formulation thereof which is effective for treating the condition and may have a sterile access port (for example the container may be an intravenous solution bag or a vial having a stopper pierceable by a hypodermic injection needle). At least one active agent in the composition is an acylsulfamide compound of the invention. The label or package insert indicates that the composition is used for treating the condition of choice, such as cancer. In one embodiment, the label or package inserts indicates that the composition comprising the acylsulfamide compound can be used to treat a thromoembolic disorder. In addition, the label or package insert may indicate that the patient to be treated is one having a thromoembolic disorder characterized by excessive bleeding. The label or package insert may also indicate that the composition can be used to treat other disorders.

The article of manufacture may comprise (a) a first container with an acylsulfamide compound contained therein; and (b) a second container with a second pharmaceutical formulation contained therein, wherein the second pharmaceutical formulation comprises a second compound with anticoagulant activity. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Typically, the inhibitors used in the method of this invention is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, and may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01–100 mg/kg, preferably about 0.1 to 20 mg/kg of patient body weight per day, with the typical initial range of compound used being 0.3 to 15 mg/kg/day.

The compound of the invention is administered by any suitable means, including oral, topical, transdermal, parenteral, subcutaneous, intraperitoneal, intrapulmonary, and intranasal, and, if desired for local immunosuppressive treatment, intralesional administration (including perfusing or otherwise contacting the graft with the inhibitor before transplantation). Parenteral infusions include intramuscular, intravenous, intraarterial, intraperitoneal, or subcutaneous administration.

Methods of Separation

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents (Eliel, E. and Wilen, S. (1994) "Stereochemistry of Organic Compounds," John Wiley & Sons, Inc.; Lochmuller, C. H., (1975) *J. Chromatogr.*, 113:(3) 283–302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375–378). Enriched or purified enantiomers can be distinguished by methods used to distinguish other chiral molecules with asymmetric carbon atoms, such as optical rotation and circular dichroism.

EXAMPLES

The invention will be more fully understood by reference to the following examples. They should not, however, be construed as limiting the scope of the invention. The following exemplary compounds were characterized and the structures determined by conventional means, including ¹H NMR and MS.

All patent and literature citations are herein incorporated by reference in their entirety.

Example 1

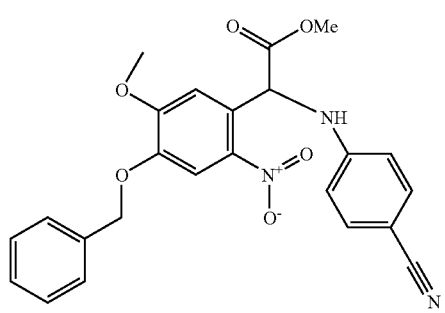

4-Benzyloxy-5-methoxy-2-nitrobenzaldehyde (12.2 g 42 mmoles) and 4-aminobenzonitrile (5 g, 42 mmoles) were dissolved in methanol (165 ml) and stirred for two hours and then heated to 60° C. for 30 minutes. The reaction was allowed to cool to room temperature and benzyl isonitrile (5 g. 42 mmoles) added. The reaction was cooled to 0° C. and boron trifluoroetherate (16 ml, 126 mmoles) added dropwise over five minutes. The reaction was stirred at 0° C. for 20 minutes and then allowed to come to room temperature and then stirred at ambient temperature for two hours. Water (4 ml) was added and the mixture stirred at room temperature overnight. A yellow precipitate was evident the next morning and the solid filtered off. The solid was washed with methanol and air dried to yield 8 grams of the desired product. The solvent from the filtrate was removed in vacuo and replaced with ethyl acetate. The solution was washed with water and saturated sodium bicarbonate, dried over anhydrous magnesium sulfate and the solvent removed. The crude material was submitted to flash chromatography (hexanes:ethyl acetate, 1:1) to yield an additional 7 g of the desired product (4-Benzyloxy-5-methoxy-2-nitro-phenyl)-(4-cyano-phenylamino)-acetic acid methyl ester. ¹HNMR (CDCl₃): 7.68 (s, 1H), 7.4 (m, 7H), 7.0 (s, 1H), 6.61 (d, 2H), 6.2 (s, 1H), 5.2 (s, 2H), 3.87 (s, 3H), 3.75 (s, 3H).

Example 2

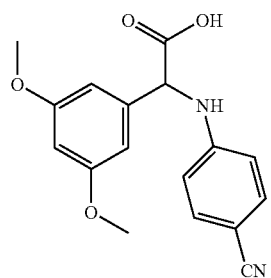

The methyl ester of the acid above (920 mg 2.85 mmoles) was suspended in 3/1 THF/water (40 ml) and cooled to 0° C. The solution was treated with 1 N LiOH (7.1 ml, 7.1 mmoles) and allowed to stir overnight. The reaction was acidified with trifluoroacetic acid until pH=4.0 was obtained. The solvent was removed in vacuo and the crude material purified by flash chromatography (ethyl acetate with 0.5% acetic acid) to yield 1 g of carboxylic acid.

Example 3

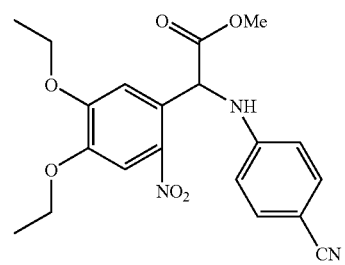

4,5-diethoxy-2-nitrobenzaldehyde (55.5 gm, 206 mmoles) and 4-aminobenzonitrile (23 g, 195 mmoles) were dissolved in methanol (700 ml) and stirred at 60° C. for 2 hours. The reaction was allowed to cool to 0° C. and tosylmethylisonitrile (45 g. 230 mmoles) added. Boron trifluoroetherate (78 ml, 620 mmoles) was added dropwise over 10 minutes. The reaction was stirred at 0° C. for 30 minutes, allowed to come to room temperature and then stirred at ambient temperature for 1.5 hours. Water (18 ml) was added and the mixture stirred at room temperature overnight. The following day the methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes:ethyl acetate, 2:1 then 1:1) to yield 46 g of the desired product (4-ethoxy-5-ethoxy-2-nitro-phenyl)-(4-cyano-phenylamino)-acetic acid methyl ester.

Example 4

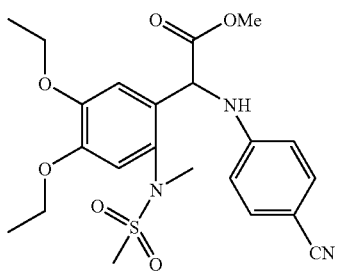

(4,5-diethoxy-2-nitro-phenyl)-(4-cyano-phenylamino)-acetic acid methyl ester (11 g, 27.5 mmole) was dissolved in ethyl acetate (300 m) and added to a flask containing 5% Pt/C (3 g) under a nitrogen atmosphere. The nitrogen was removed and replaced by hydrogen (balloon) and the reaction stirred vigorously for 6 hours. The catalyst was filtered off and the solvent removed in vacuo. The residue was taken up in dichloromethane (ca. 300 ml) and pyridine (5.6 ml, 70 mmole) added. The reaction was cooled to 0° C. and methanesulfonyl chloride (2.5 ml, 33 mmole) added dropwise. The reaction was stirred overnight. The solution was washed with water and the solvent removed in vacuo. The crude product was purified on silica using flash chromatography (Hexane:ethyl acetate 1:1) to yield 5 g of desired material—(4-cyano-phenylamino)-[4,5-diethoxy-2-(methanesulfonylamino)-phenyl]-acetic acid methyl ester. The product (4-cyano-phenylamino)-4,5-diethoxy-2-methanesulfonylamino-phenyl)-acetic acid methyl ester (5 g, 10.7 mmoles) was dissolved in dry DMF (100 ml) and cesium carbonate (7.25 g, 22 mmoles) and iodomethane (1 ml, 16 mmoles) added. The reaction was stirred at room temperature for 3 hours and the solvent removed in vacuo. The residue was taken up in ethyl acetate, acidified with 1N hydrochloric acid and the organic layer washed once with water. The material was dried over anhydrous sodium sulfate and the solvent removed in vacuo. The residue was purified by flash chromatography (hexane:ethyl acetate, 1:1) to yield 2.6 g of desired material—(4-cyano-phenylamino)-[4,5-diethoxy-2-(methanesulfonyl-methyl-amino)-phenyl]-acetic acid methyl ester.

Example 5

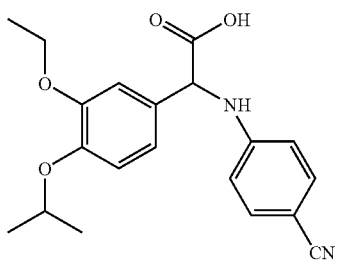

4-Isopropoxy-5-ethoxy-benzaldehyde (10.6 g 50 mmoles) and 4-aminobenzonitrile (5.9 g, 50 mmoles) were dissolved in methanol (150 ml) and stirred at 60° C. for 1.6 hours. The reaction was allowed to cool to 0° C. and tosylmethylisonitrile (9.75 g. 50 mmoles) added. Boron trifluoroetherate (19 ml, 150 mmoles) was added dropwise over 10 minutes. The reaction was stirred at 0° C. for 30 minutes, allowed to come to room temperature and then stirred at ambient temperature for 1.5 hours. Water (4.5 ml) was added and the mixture stirred at room temperature 2 days. The methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes:ethyl acetate, 1:1) to yield 12.5 g of the desired product (4-isopropoxy-5-ethoxy-phenyl)-(4-cyano-phenylamino)-acetic acid methyl ester. The product (4-isopropoxy-5-ethoxy-phenyl)-(4-cyano-phenylamino)-acetic acid methyl ester, (6 g, 16.3 mmole) was treated with 1 N LiOH (ca. 50 ml) in THF (ca. 150 ml). The reaction was stirred at room temperature for 6 hours and acidified with 1 N hydrochloric acid. The THF was removed in vacuo and the product extracted into ethyl acetate. The crude material was purified by reverse phase chromatography (ethyl acetate 3% acetic acid) to yield 4.85 g of desired acid—(4-isopropoxy-5-ethoxy-phenyl)-(4-cyano-phenylamino)-acetic acid.

Example 6

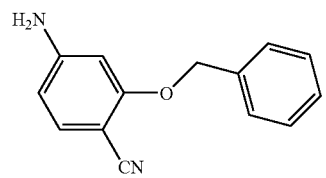

2-Hydroxy-4-nitro-benzonitrile (11.2 g, 68 mmole) was dissolved in DMF (200 ml). Potassium carbonate (11 g, 80 mmole) and benzyl bromide (9 ml, 75 mmole) were added. The reaction was stirred at room temperature overnight. The DMF was removed in vacuo and the residue taken up in ethyl acetate and water. The organic layer was separated, washed with 1 N NaOH, then with water, and dried over sodium sulfate. The crude product (5 g) was dissolved in ethyl acetate (75 ml) and added to a flask containing 5% Pt/C (500 mg). The reaction was placed under a hydrogen atmosphere (balloon) and stirred vigorously for several hours until the reaction was done (TLC). The catalyst was filtered off and the solvent removed. The product was purified by flash chromatography to yield 4.12 g of 4-amino, 2-benzyloxybenzonitrile.

Example 7

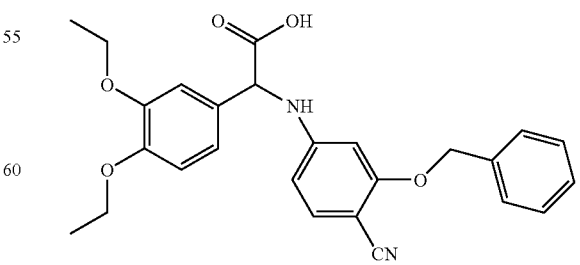

4,5-Diethoxy-benzaldehyde (3.6 g, 17.8 mmole) and 4-amino-2-benzyloxybenzonitrile (3.7 g, 17.8 mmole) were dissolved in methanol (40 ml) and stirred for 2 hours. Tosylmethylisonitrile (3.48 g. 17.8 mmoles) was added. The reaction was cooled to 0° C. and boron trifluoroetherate (6.7 ml, 54 mmoles) was added dropwise. The reaction was stirred at 0° C. for 30 minutes, allowed to come to room temperature and then stirred at ambient temperature for 3.5 hours. Water (1.6 ml) was added and the mixture stirred at room temperature 2 days. The methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes:ethyl acetate, 4:1) to yield 4.2 g of the desired product (3-benzyloxy-4-cyano-phenylamino)-3,4-ethoxy-phenyl-)-acetic acid methyl ester. The product was treated with LiOH (1.96 g) in water (50 ml) methanol (100 m), and THF (50 ml). The reaction was stirred at room temperature for 3 hours and acidified with acetic acid. The solvent was removed in vacuo and the product extracted into ethyl acetate. The crude material was purified by reverse phase chromatography (ethyl acetate 3% acetic acid) to yield 5 g of desired acid—product (3-benzyloxy-4-cyano-phenylamino)-3,4-ethoxy-phenyl-)-acetic acid.

Example 8

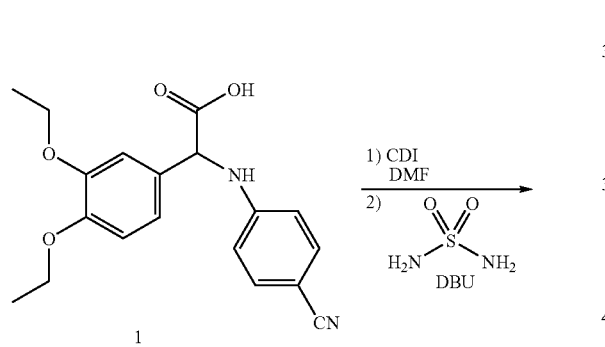

3,4-Diethoxy-N-(4-cyanophenyl)-phenylalanine (1) (500 mg, 1.47 mmol, 1.0 eq, 1,1'-carbonyldiimidazole (CDI, 2.94 mmol, 2.0 eq, Aldrich) and 15 ml of dry DMF were stirred at ambient temperature for 1.5 hrs. Sulfamide (4.41 mmol, 3.0 eq, Aldrich) was added followed by dropwise addition of 1,8-diazabicyclo[5.4.0]undec-7-ene (4.41 mmol, 3.0 eq, Fluka). The reaction was complete within minutes (tlc 50 hex, 48 EtOAc, 2 HOAc) and was poured into 10% aqueous citric acid and extracted with ethyl acetate. The ethyl acetate extract was washed with water, brine, dried over sodium sulfate and concentrated to give 650 mg of yellow foam. The product crystallized from 50 EtOAc/48 Hex/2 HOAc and was collected by filtration to give 487 mg of N-[(4-cyanophenylamino)-(3,4-diethoxyphenylacetyl)]-sulfamide (2).

Example 9

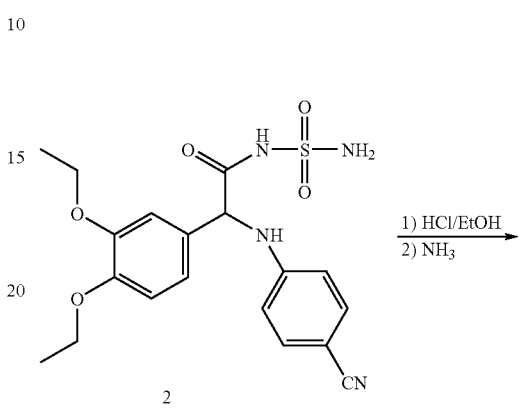

N-[(4-cyanophenylamino)-(3,4-diethoxyphenylacetyl)]-sulfamide (2) (80 mg, 0.185 mmol) was dissolved in 20 ml of ethanol pre-saturated with HCl gas at 0° C. The stirred reaction mixture was allowed to warm to ambient temperature. After two hours, the intermediate imino ester hydrochloride precipitated. The ethanol/HCl was evaporated and the solid imidate dissolved in 75 ml of a 2M solution of ammonia in methanol and stirred overnight. HPLC analysis (C-18, 25 cm, 10 to 90% acetonitrile in water, 1.5 ml/min 254 nm) indicated no remaining imidate. The solvent was evaporated and the product purified by reverse phase HPLC. Combined fractions were lyophilized to give 41 mg of 3 as the TFA salt.

Example 10

Tissue Factor/Factor VIIa Antagonist Assay

This procedure can be used to determine the constant of inhibition (Ki) for a sample compound of the invention.

Materials:

Assay Buffer: 100 mM Hepes pH 7.8, 140 mM NaCl, 0.1% PEG-8000, 0.02% Tween-80, 5 mM CaCl$_2$ Coagulation
Factor: recombinant human factor VIIa (NB #25942-16)
Cofactor: soluble Tissue Factor (1–219)
Substrate: Chromozym-tPA (Boehringer Mannheim, Cat. #1093 037) Reconstitute at 20 mM in $H_2O$. Dilute to 4 mM in assay buffer with $CaCl_2$ prior to use.
Samples: Dilute samples to 3% DMSO in assay buffer (lacking $CaCl_2$).

Procedure:
1. Prepare a solution of 2 μg/mL (90 nM) tissue factor and 1.5 μg/mL (30 nM) factor VIIa in assay buffer with $CaCl_2$.
2. Incubate for 15 minutes at room temperature.
3. Add 50 μL sample to each well.
4. Add 50 μL tissue factor/factor VIIa solution to each well.
5. Incubate for 15 minutes at room temperature with gentle agitation.
6. Add 50 μL substrate to each well.
7. Agitate plate for 20–25 sec.
8. Monitor absorbance at 405 nM every 10 sec for a total of 5 minutes at room temperature.
9. Calculate Vmax over 10 points.

Example 11

Factor Xa, Thrombin, and Plasma Kallikrein Assays

These procedures can be used to determine the constant of inhibition (Ki) for a sample compound of the invention.

Materials:
Assay Buffer: 100 mM Hepes pH 7.8, 140 mM NaCl, 0.1% PEG-8000, 0.02% Tween-80
Coagulation human Factor Xa, Thrombin, or Plasma Kallikrein (Hematologic Technologies)
Factor: Dilute to 0.45 μg/mL (9.8 nM) in assay buffer.
Substrate: S-2222, S2366 or S2302—(See below—Chromogenix Inc,) Reconstitute at 5 mM in H2O. Dilute to 1.5 mM in assay buffer prior to use.
Samples: Dilute samples to 3% DMSO in assay buffer.

Procedure:
1. Add 50 μL sample to each well.
2. Add 50 μL appropriately diluted coagulation factor to each well.
3. Incubate for 5 minutes at room temperature with gentle agitation.
4. Add 50 μL appropriately diluted substrate to each well.
5. Agitate plate for 20–25 sec.
6. Monitor absorbance at 405 nM every 10 sec for a total of 5 minutes at room temperature.
7. Calculate Vmax over 10 points.

| Assay - Enzyme, Substrate and Final Concentrations | | | | |
|---|---|---|---|---|
| Assay | TF/FVIIa | FXa | Thrombin | Plasma-Kallikrein |
| Coag Factor Final concentration | 10 nM FVIIa 30 nM TF | 3.3 nM | 8.2 nM | 1.5 nM |
| Substrate | Chromozyme tPA | S-2222 | S-2366 | S-2302 |
| Final Conc. of Substrate | 1.33 mM | 0.5 mM | 0.3 mM | 0.3 mM |

Example 12

Permeability Assay

Caco-2 or MDCK cells were maintained in Dulbecco's Modified Eagle Medium supplemented with 10% FBS, 1% penicillin/streptomycin, 1% L-glutamine, and 1% MEM non-essential amino acids solution. Cells were cultured at 37° C. in an atmosphere of 5% $CO_2$ and 95% relative humidity. Cells were passaged at 80–90% confluency using Trypsin-EDTA solution. Cells were seeded on polycarbonate Transwell® filters pre-coated with rat-tail collagen. The pore size was 0.4 μM with a growth area of 1 $cm^2$ and cells were seeded at a density of $16 \times 10^4$ cells/mL or $10 \times 10^4$ cells/mL (Caco-2 and MDCK respectively). Monolayers were rinsed with Hanks Balanced Salt Solution (HBSS) prior to starting the assay. Transport assay donor solutions were 200 μM in HBSS at pH 5.5, 6.5 or 7.4.1% DMSO or 1% Captisol was added as a solubilizing agent if necessary. Cells were incubated in a shaking water bath (35 rpm). 200 μL samples were taken from the receiver side at 0, 1.5 and 3 hours. Samples were also taken from the donor side at 0 and 3 hours. Cell layer integrity was monitored with lucifer yellow ($<1 \times 10^{-6}$ cm/sec). Lucifer yellow samples were analyzed on a CytoFluor® multi-well plate reader, Series 4000 (excitation 1: 485, emission 1: 530). All other samples were analyzed on an Agilent 1100 HPLC system using RP-HPLC and a Phenomenex C18 Luna 3μ column, 50×2.0 mm. Mobile phases were 0.1% TFA in $H_2O$ and 0.1% TFA in Acetonitrile. Permeability values in the following table represent those for the surrogate benzylnitrile compound in which the benzamidine is a benzyl nitrile.

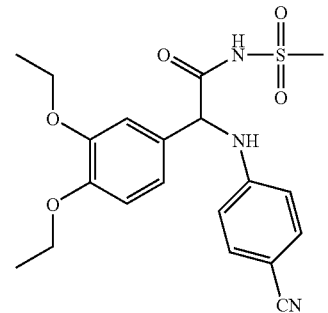

MDCK @ pH 7.4 = 0.236 $10^{-6}$ cm/sec

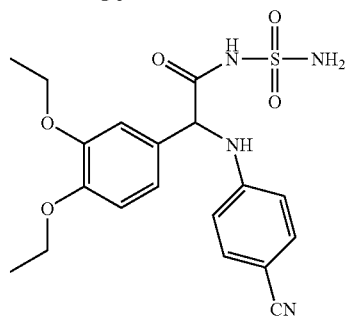

MDCK @ pH 7.4 = 1.13 $10^{-6}$ cm/sec

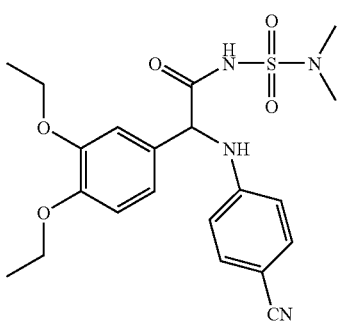

MDCK @ pH 7.4 = 1.89 10⁻⁶ cm/sec

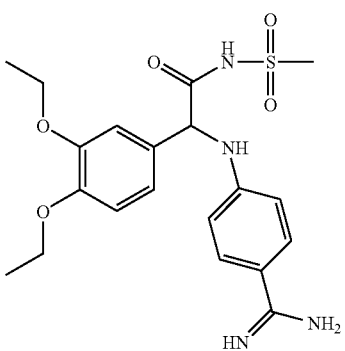

VIIa (Ki) = 0.040 μM

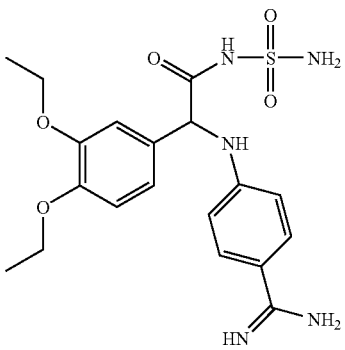

VIIa (Ki) = 0.029 μM

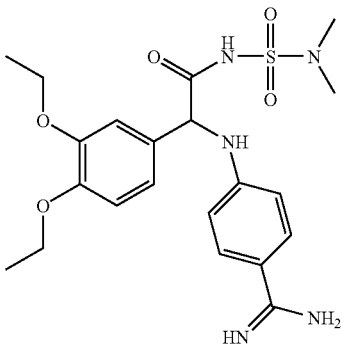

VIIa (Ki) = 0.025 μM

What is claimed is:

1. A compound having the general formula I:

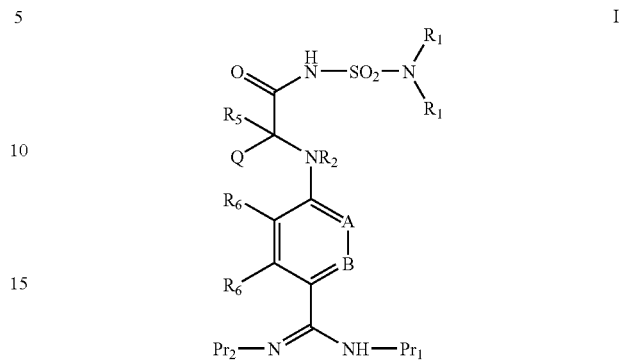

wherein

A and B are independently CH or $CR_3$;

Q is:
(1) optionally substituted alkyl having 1 to about 10 carbon atoms;
(2) optionally substituted aralkyl containing an aryl moiety having 6 to about 10 ring carbon atoms bonded to an alkyl moiety containing 1 to about 10 carbon atoms;
(3) optionally substituted carbocycloalkyl containing a carbocyclic moiety having 3 to about 10 ring carbon atoms bonded to an alkyl moiety having 1 to about 10 carbon atoms;
(4) optionally substituted alkenyl having 2 to about 10 carbon atoms;
(5) optionally substituted aralkenyl containing an aryl moiety having 5 to about 10 ring atoms bonded to an alkenyl moiety having 2 to about 10 carbon atoms;
(6) optionally substituted carbocycloalkenyl containing a carbocyclic moiety having 3 to about 10 ring carbon atoms bonded to an alkenyl moiety having 2 to about 10 carbon atoms;
(7) optionally substituted aryl having 6 to about 10 ring carbon atoms; or
(8) optionally substituted carbocyclic having 3 to about 10 ring carbon atoms;

$Pr_1$ is hydroxy, alkyl, alkoxy, alkanoyl, alkanoyloxy, alkoxycarbonyl, aryloxy, or arylalkoxy;

$Pr_2$ is H, hydroxy, alkyl, alkoxy, alkanoyl, alkanoyloxy, alkoxycarbonyl, aryloxy, or arylalkoxy;

said alkyl, alkoxy, alkanoyl, alkanoyloxy, alkoxycarbonyl, aryloxy or arylalkoxy are independently and optionally substituted with hydroxy, halogen, carboxyl, alkyl, halosubstituted alkyl, alkoxy, or a carbocycle optionally substituted with 1–5 hydroxy, alkoxy, carboxyl, alkyl, or halosubstituted alkyl; and one to three carbon atoms of said alkyl, alkoxy, alkanoyl, alkanoyloxy or alkoxycarbonyl chain are optionally replaced with O, C(O), NH, S, $SO_2$, —OC(O)—, C(O)O— or —OC(O)NH—, each $R_1$ is, independently, H, alkyl, substituted alkyl, aryl, substituted aryl, $C(O)R_7$ or $C(NH)R_7$, or both $R_1$ form a heterocycle optionally substituted with hydroxy, amino, halogen, carboxy alkyl, alkoxy, alkanoyl or alkanoyloxy;

$R_2$ is H, alkyl or substituted alkyl;

$R_3$ is H, $C_1$–$C_6$ alkyl, $C_1$–$C_6$ alkoxy, halogen or OH;

$R_5$ is selected from the group consisting of H, unsubstituted or substituted alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7$, $OC(O)R_7$, $C(O)OR_7$, $C(O)R_7$ and members in which the alkyl, $R_7$ or $R_8$ is substituted with 1–3 F, Cl, Br, I, $OR_7$, $SR_7$, $NR_7R_8$, $OC(OR_7)$, $C(O)OR_7$, $C(O)R_7$, $C(O)NR_7R_8$, $NHC(NH)NH_2$, or $PO_3$;

each $R_6$ is independently H, $C_1$–$C_6$ alkyl, $C_1$–$C_6$ alkyl-$OR_7$, $C_1$–$C_6$ alkyl-$NR_7R_8$, $C_1$–$C_6$ haloalkyl, halo, cyano, $OR_7$, $SR_7$, $NR_7R_8$, $C(O)OR_7$, $C(O)R_7$ or $OC(O)R_7$;

$R_7$ and $R_8$ are independently H or $C_1$–$C_6$ alkyl; and acid and base addition salts, and solvates thereof.

2. The compound of claim 1 wherein Q is phenyl optionally substituted with 1–5 substituents selected from the group consisting of halo, nitro, $C_1$–$C_6$ alkyl, $C_2$–$C_6$ alkenyl, $C_2$–$C_6$ alkynyl, $NR_7R_8$, $OR_7$, $SR_7$, $C_1$–$C_6$ alkyl-$C(O)OR_7$, $OC_1$–$C_6$ alkyl-$C(O)OR_7$, $C_1$–$C_6$ alkyl-$OR_7$, $OC_1$–$C_6$ alkyl-$OR_7$, $C_1$–$C_6$ alkyl-$NR_7R_8$, $OC_1$–$C_6$ alkyl-$NR_7R_8$, $C_1$–$C_6$ alkyl-$C(O)NR_7R_8$, $OC_1$–$C_6$ alkyl-$C(O)NR_7R_8$, $C_1$–$C_6$ alkyl-$C(O)R_7$, $OC_1$–$C_6$ alkyl-$C(O)R_7$, $C_1$–$C_6$ O-aralkyl, $C(O)OR_7$, $C(O)NR_7R_8$, $OC(O)NR_7R_8$, $NHC(O)R_7$, $NHC(O)NR_7R_8$, $NR_7S(O)_nR_1$, $NR_7S(O)_nR_7$, $S(O)_nR_7$, $S(O)_nNR_7$, where $R_7$ and $R_8$ independently are H or $C_1$–$C_6$ alkyl.

3. The compound of claim 1 wherein Q has the structure

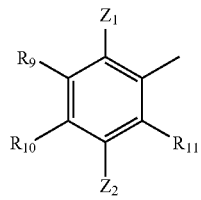

wherein $R_9$ is H, $C_1$–$C_6$ alkyl, $C_2$–$C_6$ alkenyl, $C_2$–$C_6$ alkynyl, $C_1$–$C_6$ alkoxy, hydroxy, $NR_7R_8$, $SR_7$ or $OR_7$, where $R_7$ and $R_8$, independently, are H or unsubstituted or substituted $C_1$–$C_6$ alkyl;

$R_{10}$, $R_{11}$ and $Z_2$, are each independently selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-$C(O)R_7$, $C_1$–$C_6$ alkyl-$C(O)NR_7R_8$, $C_1$–$C_6$ alkyl-$C(O)OR_7$, $C_1$–$C_6$ alkyl-$OC(O)R_7$, $C_1$–$C_6$ alkyl-$OR_7$, $OC_1$–$C_6$ alkyl-$C(O)R_7$, $OC_1$–$C_6$ alkyl-$C(O)OR_7$, $OC_1$–$C_6$ alkyl-$OC(O)R_7$, $OC$—$C_1$–$C_6$ alkyl-$OR_7$, $OC_1$–$C_6$ alkyl-$C(O)NR_7R_8$, $C_1$–$C_6$ haloalkyl, $OR_{12}$, $C_1$–$C_6$ alkyl-$R_{12}$, $O$—$C_1$–$C_6$ alkyl-$R_{12}$, $C(O)OR_7$, $C(O)OR_{12}$, $C(O)NR_7R_8$, $OC(O)NR_7R_8$, $NR_7C(O)R_7$, $NR_7C(O)R_{12}$, $NR_7C(O)$—$NR_7R_8$, $NR_7$—$(C_1$–$C_6$ alkyl)-$C(O)$—$NR_7R_8$, $NR_7C(O)OR_7$, $NR_7C(O)OR_{12}$, $NR_7S(O)n$-$R_1$, $NR_7S(O)n$-$R_7$ and $NR_7S(O)n$-$R_{12}$, wherein $R_7$ and $R_8$ are independently H or unsubstituted or substituted $C_1$–$C_6$ alkyl; $R_{12}$ is unsubstituted or substituted $C_6$–$C_{10}$ aryl; and n is 1 or 2; and $Z_1$ is H, $C_1$–$C_6$ alkyl, $C_1$–$C_6$ alkoxy, halogen or nitro.

4. The compound of claim 3 wherein $R_{10}$ is selected from the group consisting of $C_1$–$C_6$ alkyl, $C_1$–$C_6$ alkoxy, $C_1$–$C_6$ aminoalkyl, $C_1$–$C_6$ haloalkyl, $C_1$–$C_6$ hydroxyalkyl, phenyl, phenoxy, benzyl, benzyloxy, where phenoxy and benzyloxy are optionally substituted with $C_1$–$C_6$ alkyl, $C_1$–$C_6$ alkoxy, halo, $C_1$–$C_6$ haloalkyl, $C_1$–$C_6$ hydroxyalkyl, $C_1$–$C_6$ aminoalkyl, $OC(O)$—$C_1$–$C_6$ alkyl, $C(O)O$—$C_1$–$C_6$ alkyl and $C(O)OH$.

5. The compound of claim 3 wherein $R_{11}$ is $NR_7$—$(C_1$–$C_6$ alkyl)-$C(O)$—$NR_7R_8$, $NR_7S(O)n$-$R_7$ or $NR_7S(O)n$-$R_{12}$ where n is 1 or 2.

6. The compound of claim 3 wherein $Z_1$ and $Z_2$ are hydrogen, and $R_{10}$ is $OR_7$, $OR_{12}$, $O$—$(C_7$–$C_{10}$-aralkyl), $OC_1$–$C_6$ alkyl-$OR_7$ or $OC_1$–$C_6$ alkyl-$OR_{12}$.

7. The compound of claim 3 wherein $Z_1$ or $Z_2$ is $C_1$–$C_6$ alkyl, $C_1$–$C_6$ alkoxy, halogen or nitro.

8. The compound of claim 3 wherein $R_{10}$ is $OR_7$, $OR_{12}$, $C_1$–$C_6$ alkyl-$OR_7$ or $C_1$–$C_6$ alkyl-$OR_{12}$.

9. The compound of claim 3 wherein $R_{11}$ is $NR_7S(O)_n$—$R_7$ or $NR_7S(O)_n$—$R_{12}$, and n is 1 or 2.

10. The compound of claim 1 wherein each $R_1$ is independently selected from the group consisting of $C_1$–$C_6$ alkyl, $C_2$–$C_6$ alkenyl, $C_2$–$C_6$ alkynyl, $C_3$–$C_6$ cycloalkyl, phenyl, naphthyl, benzyl and heteroaryl having 5–6 ring atoms selected from carbon atoms and 1–2 heteroatoms, where the heteroatoms are N, S, or O, and $R_1$ is optionally substituted with 1–3 substituents selected from the group consisting of halo, nitro, $C_1$–$C_6$ alkyl, $NR_7R_8$, $OR_7$, $SR_7$, $C_1$–$C_6$ alkyl-$C(O)R_7$, $C_1$–$C_6$ alkyl-$OC(O)R_7$, $C_1$–$C_6$ alkyl-$C(O)R_7$, $C_1$–$C_6$ alkyl-$OR_7$, $C_1$–$C_6$ haloalkyl, $C_1$–$C_6$ alkyl-$NR_7R_8$, $C(O)OR_7$, $OC(O)R_7$, $C(O)NR_7R_8$, $OC(O)NR_7R_8$, $NHC(O)R_7$, and $NHC(O)NR_7R_8$, where $R_7$ and $R_8$ independently are H or $C_1$–$C_6$ alkyl.

11. The compound of claim 1 wherein A and B are CH.

12. The compound of claim 1 wherein both $R_6$ substituents are H.

13. The compound of claim 1 wherein both $R_1$ substituents are H, methyl or together with the nitrogen atom from which they depend form a morpholino heterocycle.

14. The compound of claim 1 wherein $Pr_1$ is hydroxy, alkoxy, alkanoyl, aryloxy or aryl; wherein said alkoxy, alkanoyl, aryloxy and aryl are optionally substituted with halogen; and $Pr_2$ is H.

15. A pharmaceutical composition comprising an effective amount of the compound of claim 1, or a pharmaceutically acceptable salt thereof, and a pharmaceutically acceptable diluent, carrier or excipient.

16. The pharmaceutical composition of claim 15 formulated in a unit dosage form.

17. The pharmaceutical composition of claim 15 administered orally.

18. The pharmaceutical composition of claim 15 administered parenterally.

* * * * *